(12) United States Patent
Cao et al.

(10) Patent No.: US 11,666,295 B2
(45) Date of Patent: Jun. 6, 2023

(54) METHOD OF PHASE CONTRAST IMAGING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 17/863,676

(22) Filed: Jul. 13, 2022

(65) Prior Publication Data

US 2022/0346737 A1 Nov. 3, 2022

Related U.S. Application Data

(63) Continuation of application No. PCT/CN2020/076913, filed on Feb. 27, 2020.

(51) Int. Cl.
*A61N 5/10* (2006.01)
*A61B 6/00* (2006.01)

(52) U.S. Cl.
CPC .............. *A61B 6/484* (2013.01); *A61B 6/502* (2013.01)

(58) Field of Classification Search
CPC ....... A61B 6/4208; A61B 6/4233; A61B 6/52; A61B 6/5258; A61B 6/5264; A61B 6/585; A61B 6/583; A61B 6/4241; A61B 6/42; A61B 6/06; A61B 6/584; A61B 6/64266; A61B 6/547; A61B 6/582; A61B 6/256; G01N 21/47975; G01N 2223/1016; G01N 23/20
See application file for complete search history.

(56) References Cited

FOREIGN PATENT DOCUMENTS

| CN | 109906388 A | 6/2019 | |
|---|---|---|---|
| CN | 109975334 A | 7/2019 | |
| CN | 110022770 A | 7/2019 | |
| JP | 2005337878 A | 12/2005 | |
| JP | 2008046130 A | * 2/2008 | ............. G01N 23/20 |
| TW | 201907155 A | 2/2019 | |
| TW | 201917419 A | 5/2019 | |

* cited by examiner

*Primary Examiner* — Don K Wong
(74) *Attorney, Agent, or Firm* — IPro, PLLC; Qian Gu

(57) ABSTRACT

Disclosed herein is a method, comprising: for i=1, ..., M, sending a pencil radiation beam (i) toward an image sensor, wherein the pencil radiation beam (i) is incident on an incident region (i) on the image sensor, wherein the pencil radiation beam (i) is aimed at a target region (i) on the image sensor, wherein M is a positive integer, wherein the image sensor comprises active areas spatially discontinuous from each other, and wherein the incident regions (i), i=1, ..., M and the target regions (i), i=1, ..., M are on the active areas; and for i=1, ..., M, determining an offset (i) between the incident region (i) and the target region (i).

18 Claims, 28 Drawing Sheets

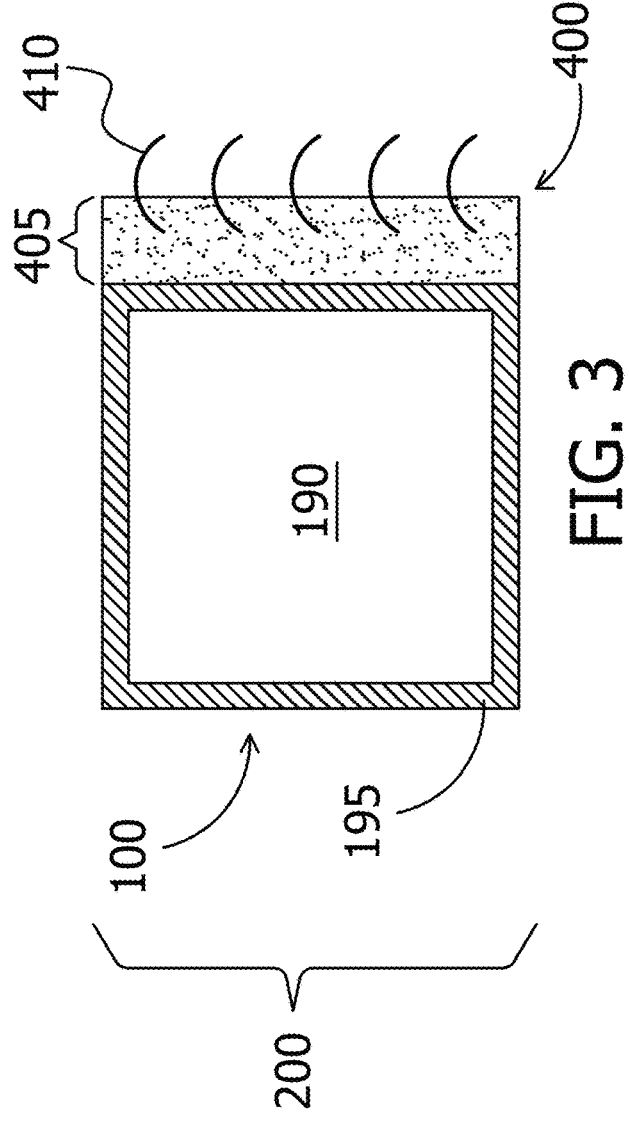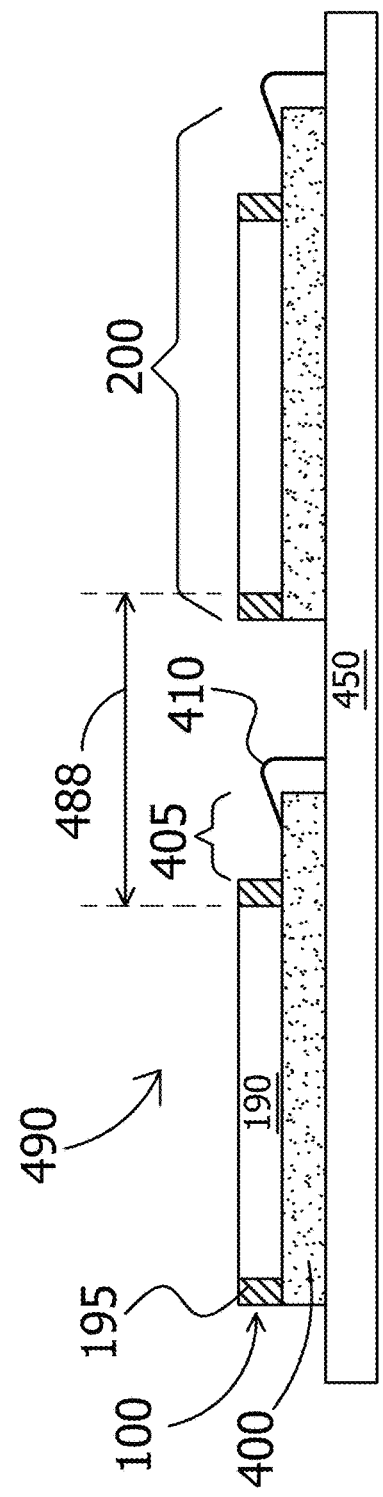

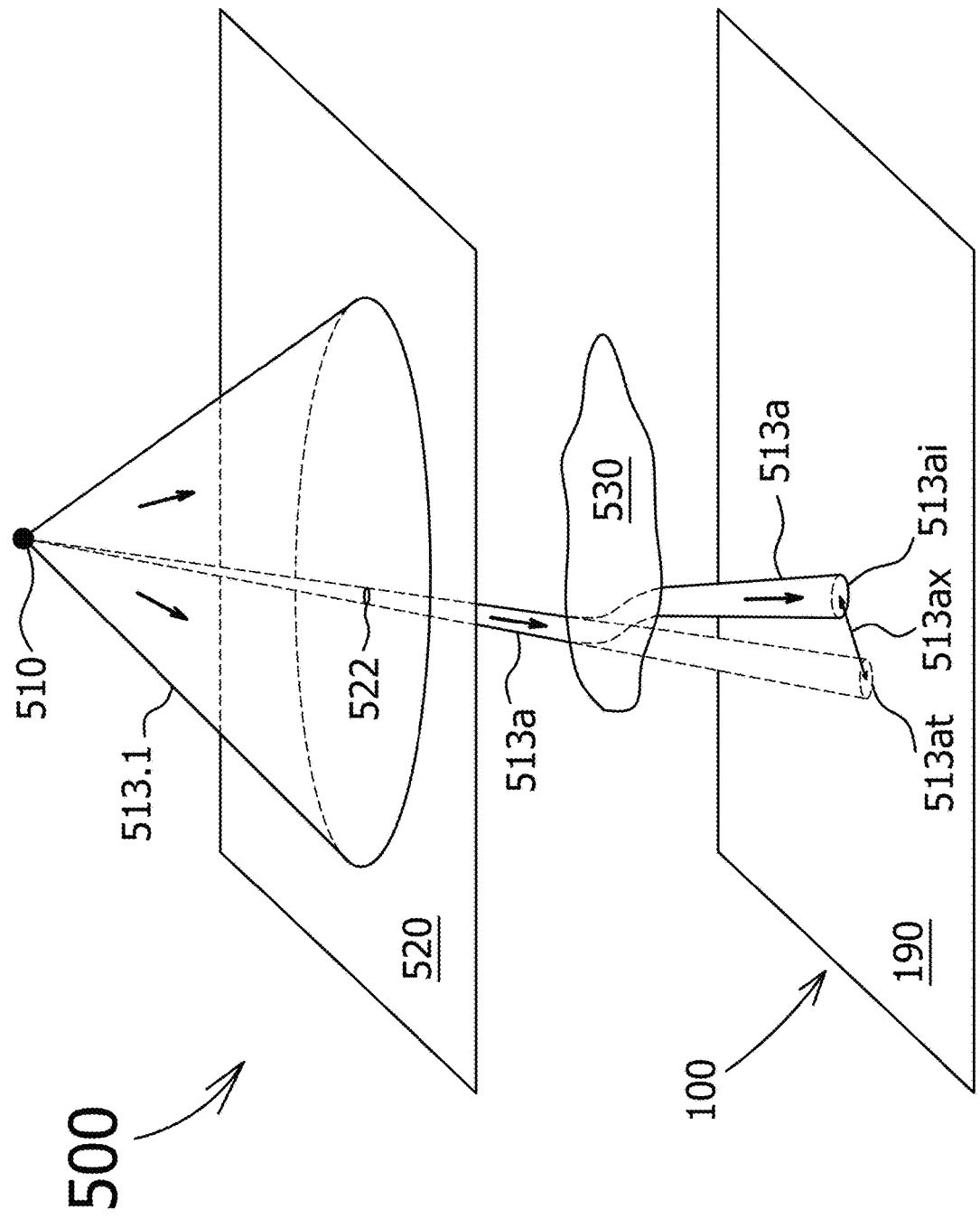

580

582: for i=1,...,M, sending a pencil radiation beam (i) incident on an incident region (i) on the active area 190 of the radiation detector 100, wherein the pencil radiation beam (i) is aimed at a target region (i) on the active area 190.

584: for i=1,...,M, determining an offset (i) between the incident region (i) and the target region (i).

FIG. 5C

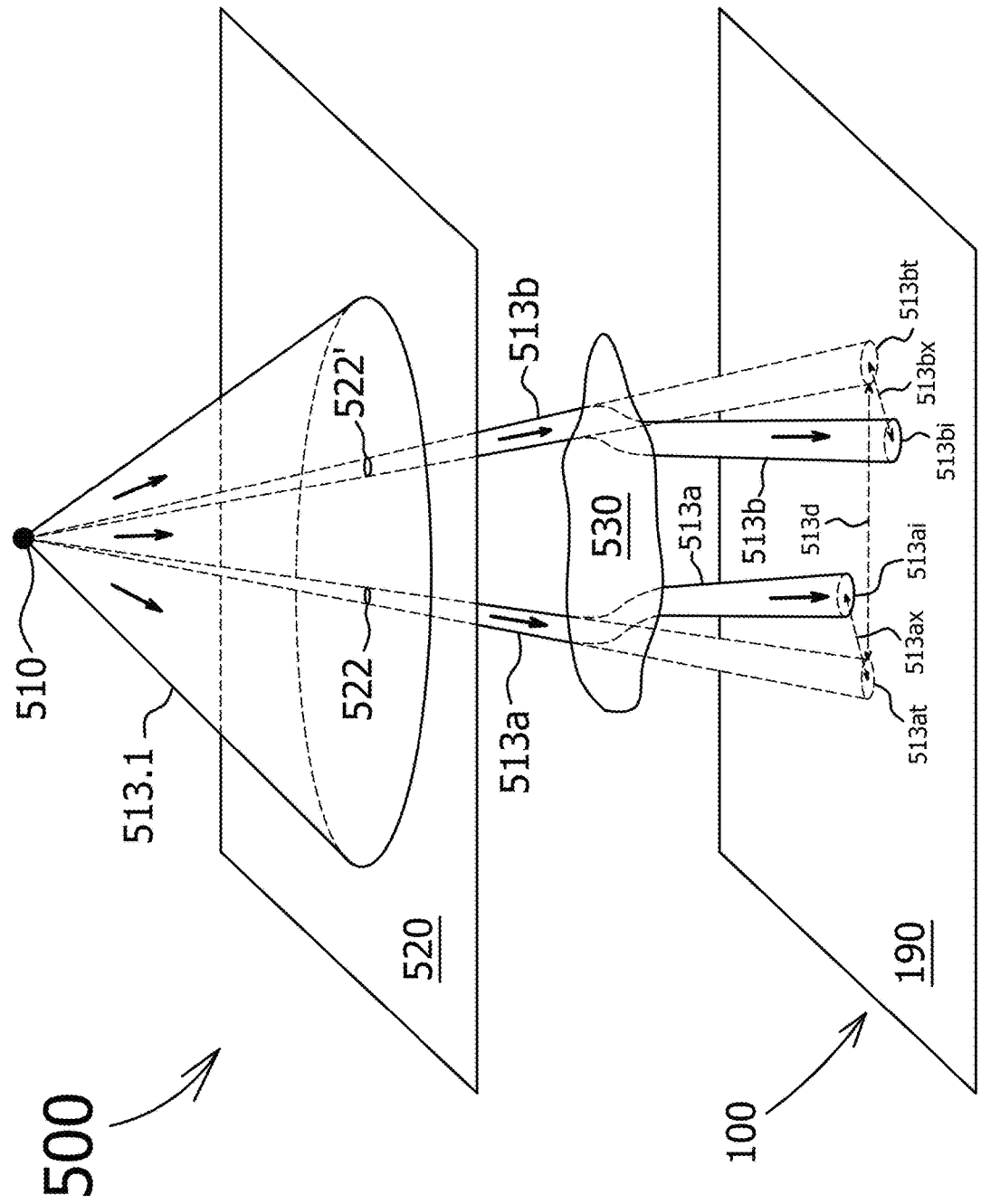

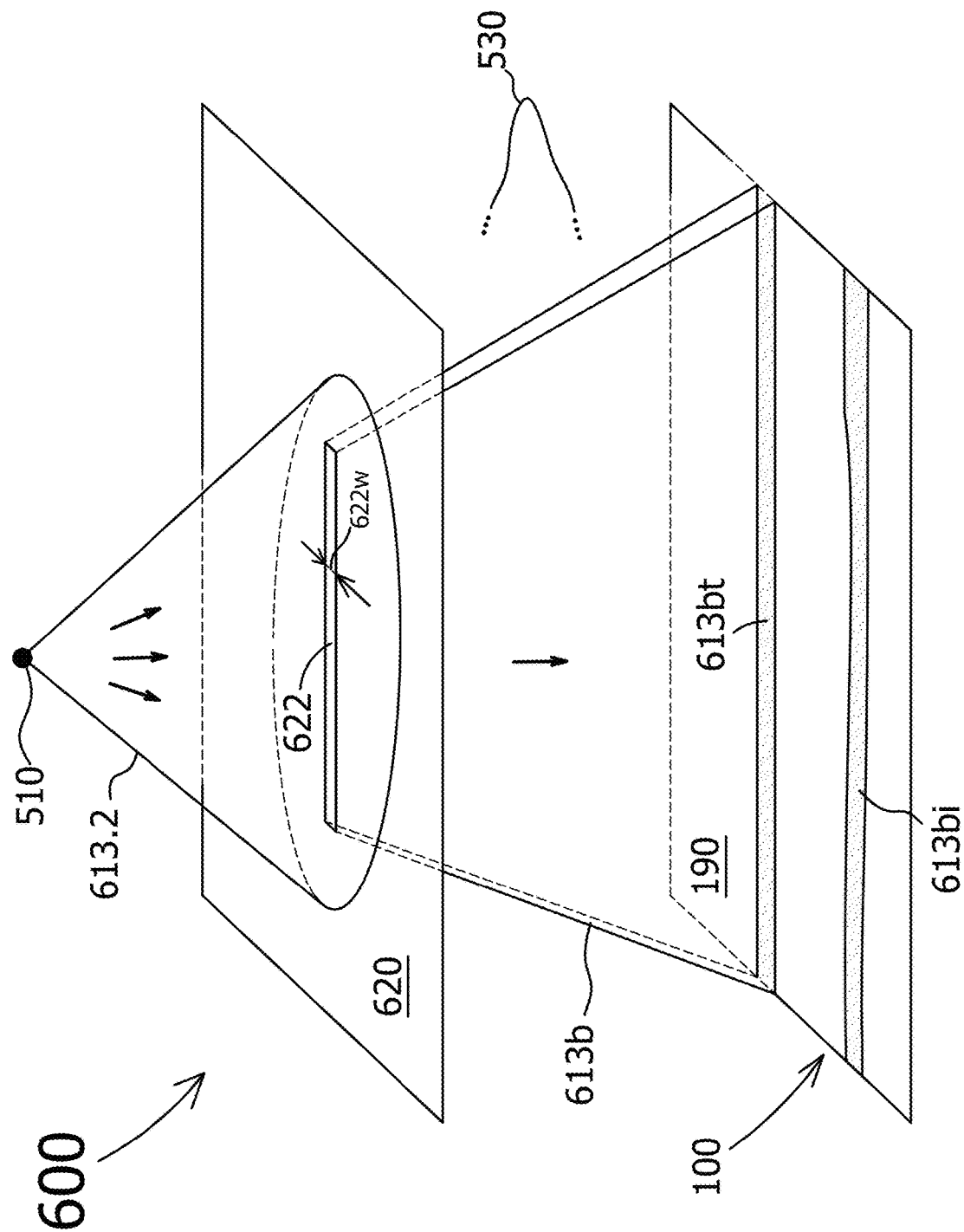

682: sending first fan radiation beams and second fan radiation beams incident on the active area 190 of the radiation detector 100, wherein for i=1,...,M, a pair (i) of one of the first fan radiation beams and one of the second fan radiation beams are incident on two incident regions on the active area 190, the two incident regions sharing a common incident region (i) on the active area 190, and wherein the pair (i) are aimed at two target regions on the active area 190, the two target regions sharing a common target region (i) on the active area 190.

684: for i=1,...,M, determining an offset (i) between the common incident region (i) and the common target region (i).

FIG. 6F

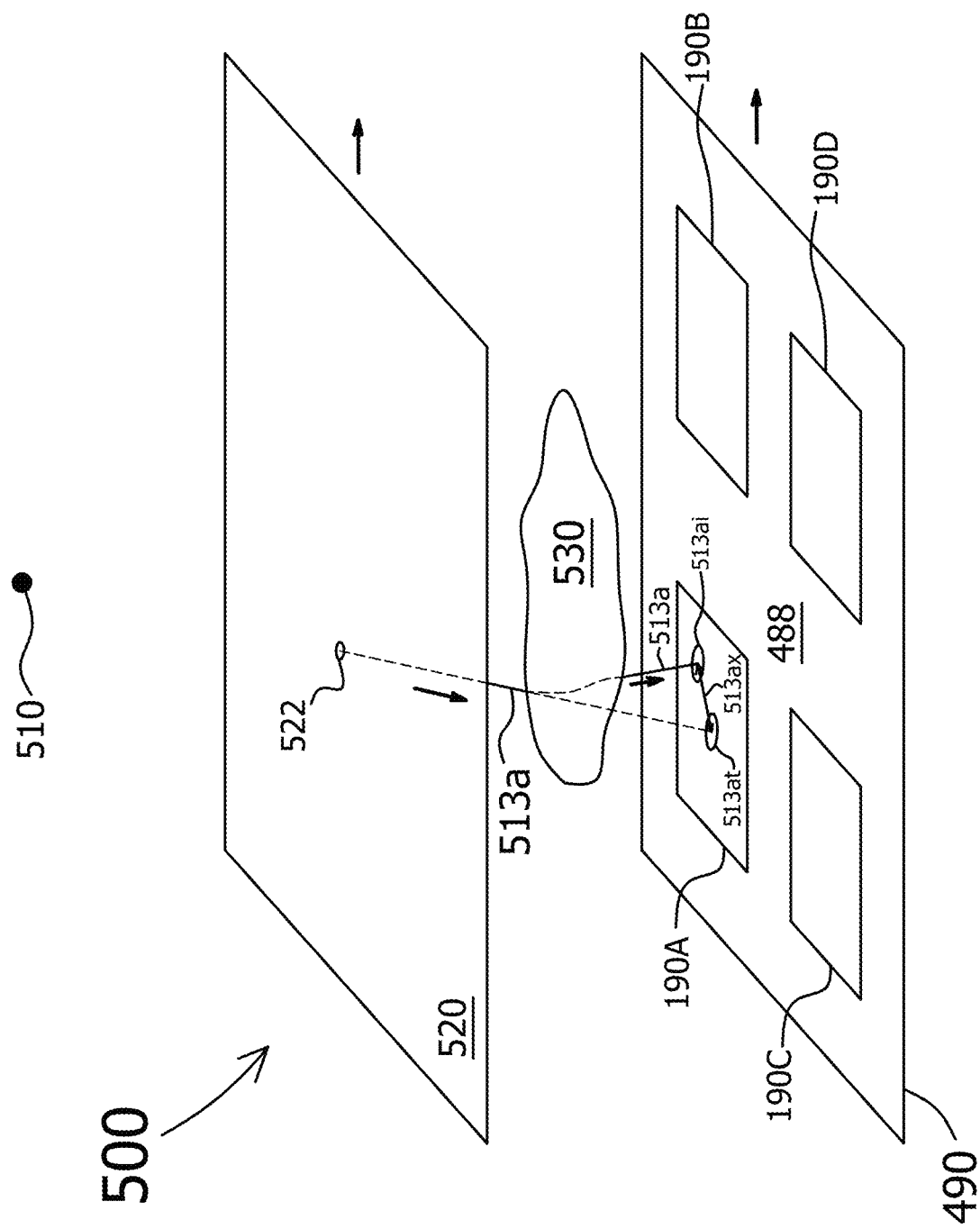

980

982: for i=1,...,M, sending a pencil radiation beam (i) incident on an incident region (i) on the image sensor 490, wherein the pencil radiation beam (i) is aimed at a target region (i) on the image sensor 490, wherein the image sensor 490 comprises P active areas 190 physically separated from each other, and wherein the incident regions (i), i=1,...,M and the target regions (i), i=1,...,M are on the P active areas 190.

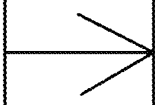

984: for i=1,...,M, determining an offset (i) between the incident region (i) and the target region (i).

FIG. 9D

992: sending first fan radiation beams and second fan radiation beams incident on the image sensor 490, wherein for i=1,...,M, a pair (i) of one of the first fan radiation beams and one of the second fan radiation beams are incident on two incident regions on the image sensor 490, the two incident regions sharing a common incident region (i) on the image sensor 490, and wherein for i=1,...,M, the pair (i) are aimed at two target regions on the image sensor 490, the two target regions sharing a common target region (i) on the image sensor 490, wherein the image sensor 490 comprises P active areas 190 physically separated from each other, wherein the common incident regions (i), i=1,...,M and the common target regions (i), i=1,...,M are on the P active areas 190.

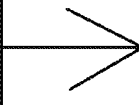

994: for i=1,...,M, determining an offset (i) between the common incident region (i) and the common target region (i).

FIG. 9E ns. An imaging system may include multiple radiation
METHOD OF PHASE CONTRAST IMAGING

BACKGROUND

A radiation detector is a device that measures a property of a radiation. Examples of the property may include a spatial distribution of the intensity, phase, and polarization of the radiation. The radiation may be one that has interacted with an object. For example, the radiation measured by the radiation detector may be a radiation that has penetrated the object. The radiation may be an electromagnetic radiation such as infrared light, visible light, ultraviolet light, X-ray or γ-ray. The radiation may be of other types such as α-rays and β-rays. An imaging system may include multiple radiation detectors.

SUMMARY

Disclosed herein is a method, comprising: for i=1, . . . , M, sending a pencil radiation beam (i) toward an image sensor, wherein the pencil radiation beam (i) is incident on an incident region (i) on the image sensor, wherein the pencil radiation beam (i) is aimed at a target region (i) on the image sensor, wherein M is a positive integer, wherein the image sensor comprises active areas spatially discontinuous from each other, and wherein the incident regions (i), i=1, . . . , M and the target regions (i), i=1, . . . , M are on the active areas; and for i=1, . . . , M, determining an offset (i) between the incident region (i) and the target region (i).

In an aspect, the method further comprises determining a refractive index for a point (i), i=1, . . . , M, of an object based on the offset (i) and a position of the target region (i) relative to the object; wherein the pencil radiation beam (i) is incident on the point (i).

In an aspect, each of the target regions (i), i=1, . . . , M, is not smaller than a pixel of the image sensor.

In an aspect, any two of the target regions (i), i=1, . . . , M, at the same time are spaced apart by at least 10 times of a width of a pixel of the image sensor.

In an aspect, the pencil radiation beams (i), i=1, . . . , M, are formed by directing radiation through at least a pinhole of a filter, and wherein the method further comprises moving the filter and the image sensor between multiple exposures such that target regions on the image sensor the pencil radiation beams (i) are aimed at remain the same relative to the image sensor across the multiple exposures.

In an aspect, the method further comprises: capturing images of the pencil radiation beams (i), i=1, . . . , M, determining a position (i) of the incident region (i) based on the captured image of the pencil radiation beam (i), wherein said determining the offset (i) is based on the position (i) of the incident region (i).

In an aspect, the method further comprises: for i=1, . . . , M, sending additional pencil radiation beams (i, j), j=1, . . . , Ni, wherein Ni is a positive integer, and wherein each of the additional pencil radiation beams (i, j), j=1, . . . , Ni is parallel to and overlaps the pencil radiation beam (i); capturing images of the pencil radiation beams (i), i=1, . . . , M and the additional pencil radiation beams (i, j), i=1, . . . , M, and j=1, . . . , Ni; and for i=1, . . . , M, applying a super resolution algorithm to the image of the pencil radiation beam (i) and the images of the additional pencil radiation beams (i, j), j=1, . . . , Ni thereby resulting in an enhanced image (i) of the pencil radiation beam (i), determining a position (i) of the incident region (i) based on the enhanced image (i), wherein said determining the offset (i) is based on the position (i) of the incident region (i).

Disclosed herein is a method, comprising: sending first fan radiation beams and second fan radiation beams toward an image sensor, wherein for i=1, . . . , M, a pair (i) of one of the first fan radiation beams and one of the second fan radiation beams are respectively incident on two incident regions on the image sensor, the two incident regions sharing a common incident region (i) on the image sensor, wherein M is a positive integer, wherein for i=1, . . . , M, the pair (i) are respectively aimed at two target regions on the image sensor, the two target regions sharing a common target region (i) on the image sensor, wherein the image sensor comprises active areas spatially discontinuous from each other, and wherein the common incident regions (i), i=1, . . . , M and the common target regions (i), i=1, . . . , M are on the active areas; and for i=1, . . . , M, determining an offset (i) between the common incident region (i) and the common target region (i).

In an aspect, the method further comprises: determining a refractive index for a point (i), i=1, . . . , M, of an object based on the offset (i) and a position of the common target region (i) relative to the object, wherein both fan radiation beams of the pair (i) are incident on the point (i).

In an aspect, each of the common target regions (i), i=1, . . . , M, is not smaller than a pixel of the image sensor.

In an aspect, any two target regions on the image sensor any two beams of the first fan radiation beams are aimed at the same time are spaced apart by at least 10 times of a width of a pixel of the image sensor.

In an aspect, target regions on the image sensor aimed at by the first fan radiation beams are parallel to each other.

In an aspect, the first fan radiation beams are formed by directing radiation through least a slit of a filter, and the method further comprises moving the filter and the image sensor between multiple exposures such that target regions on the image sensor the first fan radiation beams are aimed at remain the same relative to the image sensor across the multiple exposures.

In an aspect, target regions on the image sensor the first fan radiation beams are aimed at are not parallel to target regions on the image sensor the second fan radiation beams are aimed at.

In an aspect, wherein the first fan radiation beams are formed by directing radiation through first slits of a filter and the second fan radiation beams are formed by directing radiation through second slits of the filter, and wherein the first slits are parallel to one another, the second slits are parallel to one another and the first slits are not parallel to the second slits.

In an aspect, the method further comprises: capturing images of the first and second fan radiation beams, determining a position (i) of the common incident region (i) based on captured images of the two beams of the pair (i), wherein said determining the offset (i) is based on the position (i) of the common incident region (i).

In an aspect, the method further comprises: for each beam of the first and second fan radiation beams, sending additional fan radiation beams parallel to and overlapping said beam of the first and second fan radiation beams; capturing images of the first and second fan radiation beams and their associated additional fan radiation beams; and for each beam of the first and second fan radiation beams, applying a super resolution algorithm to the image of said beam and the images of the additional fan radiation beams associated with said beam thereby resulting in an enhanced image of said beam, determining a position (i) of the common incident region (i) based on the enhanced images of the two beams of the pair (i), wherein said determining the offset (i) is based on the position (i) of the common incident region (i).

In an aspect, the second fan radiation beams are sent after the first fan radiation beams are sent.

BRIEF DESCRIPTION OF FIGURES

FIG. 3 schematically shows a top view of a package including the radiation detector and a printed circuit board (PCB).

FIG. 4 schematically shows a cross-sectional view of an image sensor, where a plurality of the packages of FIG. 3 are mounted to a system PCB, according to an embodiment.

FIG. 5A-FIG. 5D schematically show an imaging system and its operation using pencil radiation beams, according to different embodiments.

FIG. 6A-FIG. 6F schematically show an imaging system and its operation using fan radiation beams, according to different embodiments.

FIG. 8A-FIG. 8C schematically show the imaging system 500 and its operation using the image sensor, according to different embodiments.

FIG. 9D & FIG. 9E respectively show two flowcharts summarizing and generalizing the operations of the imaging systems 500 and 600 using the image sensor, according to different embodiments.

DETAILED DESCRIPTION

Figure 1:
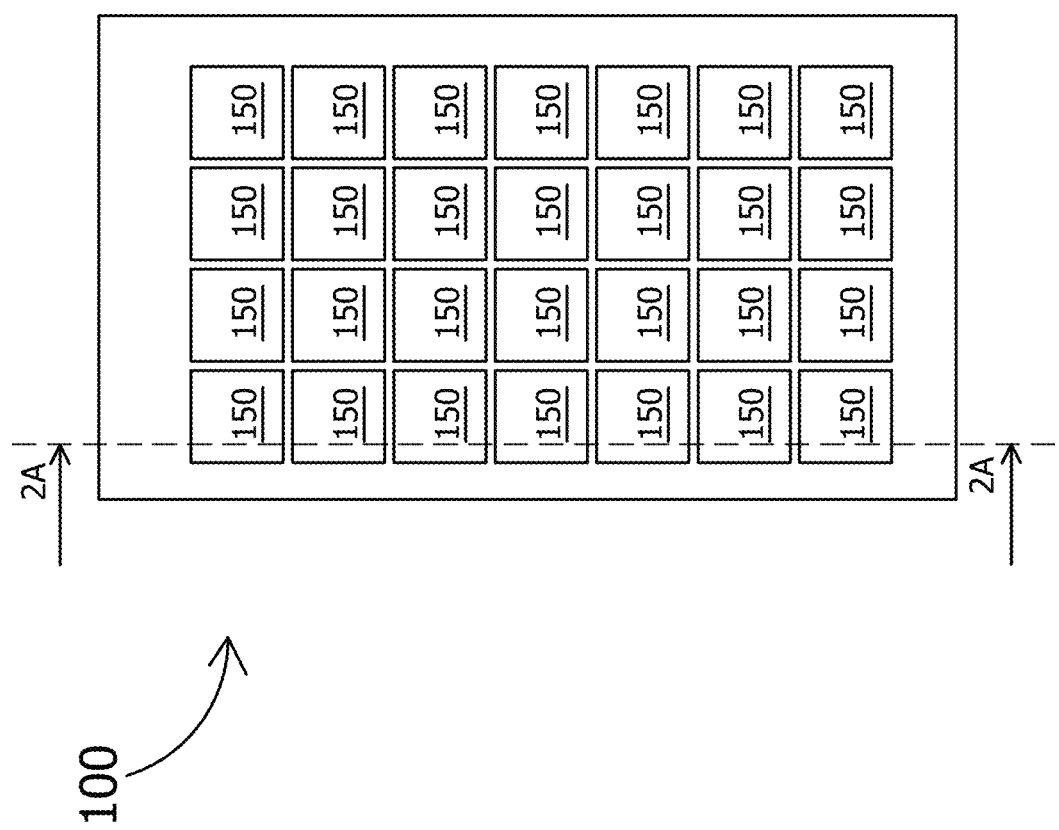
FIG. 1 schematically shows a radiation detector, according to an embodiment.

FIG. 1 schematically shows a radiation detector 100, as an example. The radiation detector 100 includes an array of pixels 150 (also referred to as sensing elements 150). The array may be a rectangular array (as shown in FIG. 1), a honeycomb array, a hexagonal array or any other suitable array. The array of pixels 150 in the example of FIG. 1 has 7 rows and 4 columns; however, in general, the array of pixels 150 may have any number of rows and any number of columns.

Each pixel 150 may be configured to detect radiation from a radiation source (not shown) incident thereon and may be configured to measure a characteristic (e.g., the energy of the particles, the wavelength, and the frequency) of the radiation. A radiation may include particles such as photons (electromagnetic waves) and subatomic particles. Each pixel 150 may be configured to count numbers of particles of radiation incident thereon whose energy falls in a plurality of bins of energy, within a period of time. All the pixels 150 may be configured to count the numbers of particles of radiation incident thereon within a plurality of bins of energy within the same period of time. When the incident particles of radiation have similar energy, the pixels 150 may be simply configured to count numbers of particles of radiation incident thereon within a period of time, without measuring the energy of the individual particles of radiation.

Each pixel 150 may have its own analog-to-digital converter (ADC) configured to digitize an analog signal representing the energy of an incident particle of radiation into a digital signal, or to digitize an analog signal representing the total energy of a plurality of incident particles of radiation into a digital signal. The pixels 150 may be configured to operate in parallel. For example, when one pixel 150 measures an incident particle of radiation, another pixel 150 may be waiting for a particle of radiation to arrive. The pixels 150 may not have to be individually addressable.

The radiation detector 100 described here may have applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this radiation detector 100 in place of a photographic plate, a photographic film, a PSP plate, an X-ray image intensifier, a scintillator, or another semiconductor X-ray detector.

Figure 2A:
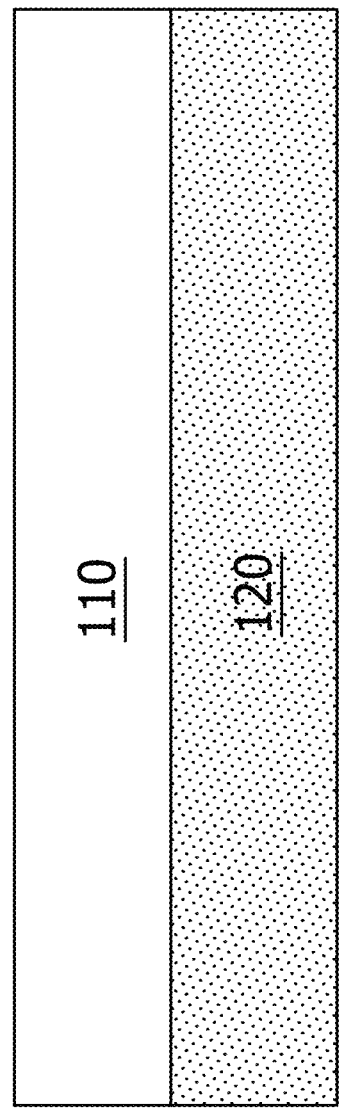
FIG. 2A schematically shows a simplified cross-sectional view of the radiation detector.

FIG. 2A schematically shows a simplified cross-sectional view of the radiation detector 100 of FIG. 1 along a line 2A-2A, according to an embodiment. More specifically, the radiation detector 100 may include a radiation absorption layer 110 and an electronics layer 120 (e.g., an ASIC) for processing or analyzing electrical signals which incident radiation generates in the radiation absorption layer 110. The radiation detector 100 may or may not include a scintillator (not shown). The radiation absorption layer 110 may include a semiconductor material such as, silicon, germanium, GaAs, CdTe, CdZnTe, or a combination thereof. The semiconductor material may have a high mass attenuation coefficient for the radiation of interest.

Figure 2B:
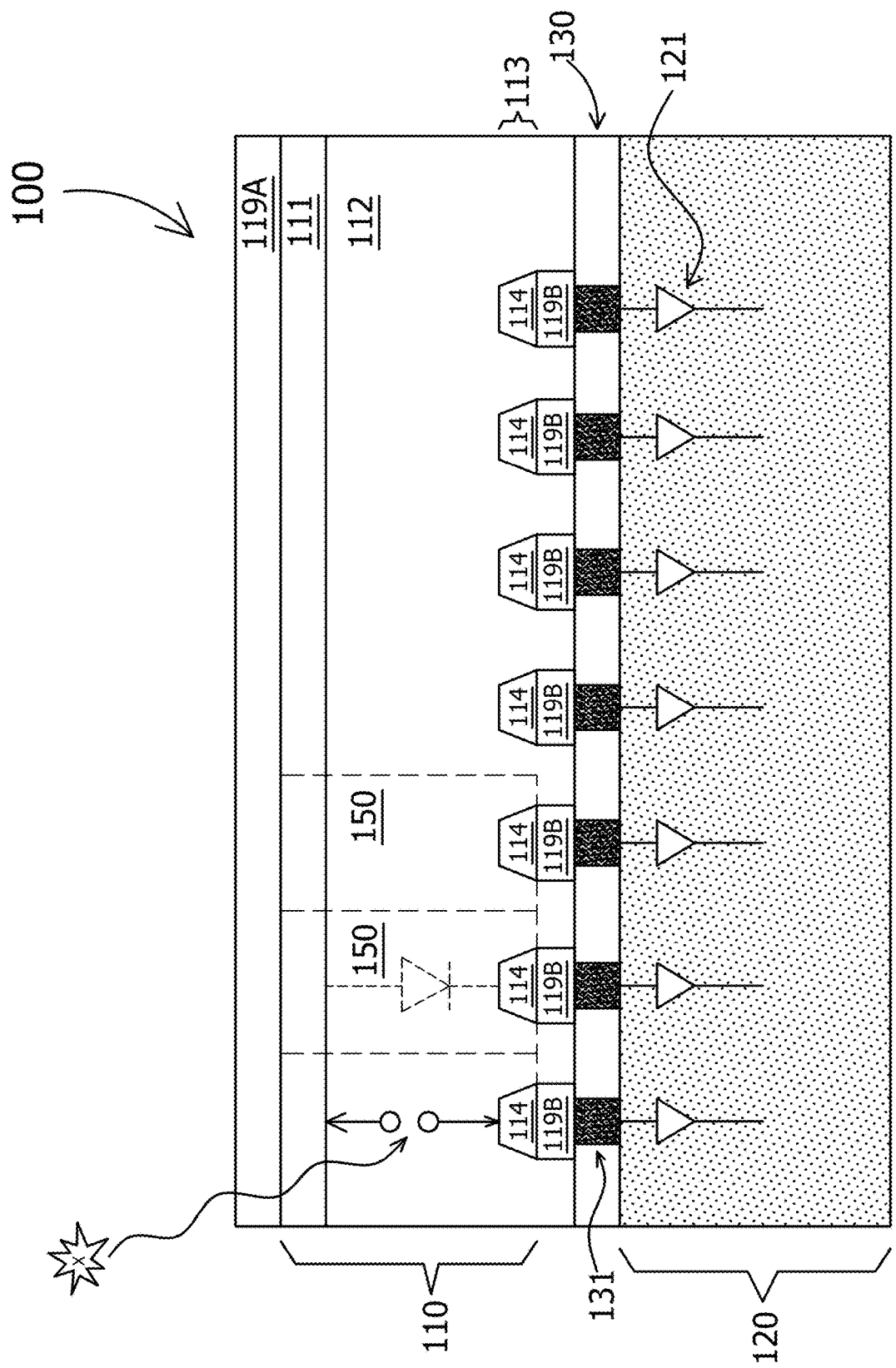
FIG. 2B schematically shows a detailed cross-sectional view of the radiation detector.

FIG. 2B schematically shows a detailed cross-sectional view of the radiation detector 100 of FIG. 1 along the line 2A-2A, as an example. More specifically, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example of FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes (more specifically, 7 diodes corresponding to 7 pixels 150 of one row in the array of FIG. 1, of which only 2 pixels 150 are labeled in FIG. 2B for simplicity). The plurality of diodes have an electrode 119A as a shared (common) electrode. The first doped region 111 may also have discrete portions.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessor, and memory. The electronic system 121 may include one or more ADCs. The electronic system 121 may include components shared by the pixels 150 or components dedicated to a single pixel 150. For example, the electronic system 121 may include an amplifier dedicated to each pixel 150 and a microprocessor shared among all the pixels 150. The electronic system 121 may be electrically connected to the pixels 150 by vias 131. Space among the vias may be filled with a filler material 130, which may increase the mechanical stability of the connection of the electronics layer 120 to the radiation absorption layer 110. Other bonding techniques are possible to connect the electronic system 121 to the pixels 150 without using the vias 131.

When radiation from the radiation source (not shown) hits the radiation absorption layer 110 including diodes, particles of the radiation may be absorbed and generate one or more charge carriers (e.g., electrons, holes) by a number of mechanisms. The charge carriers may drift to the electrodes of one of the diodes under an electric field. The field may be an external electric field. The electrical contact 119B may include discrete portions each of which is in electrical contact with the discrete regions 114. The term "electrical contact" may be used interchangeably with the word "electrode." In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel 150.

Figure 2C:
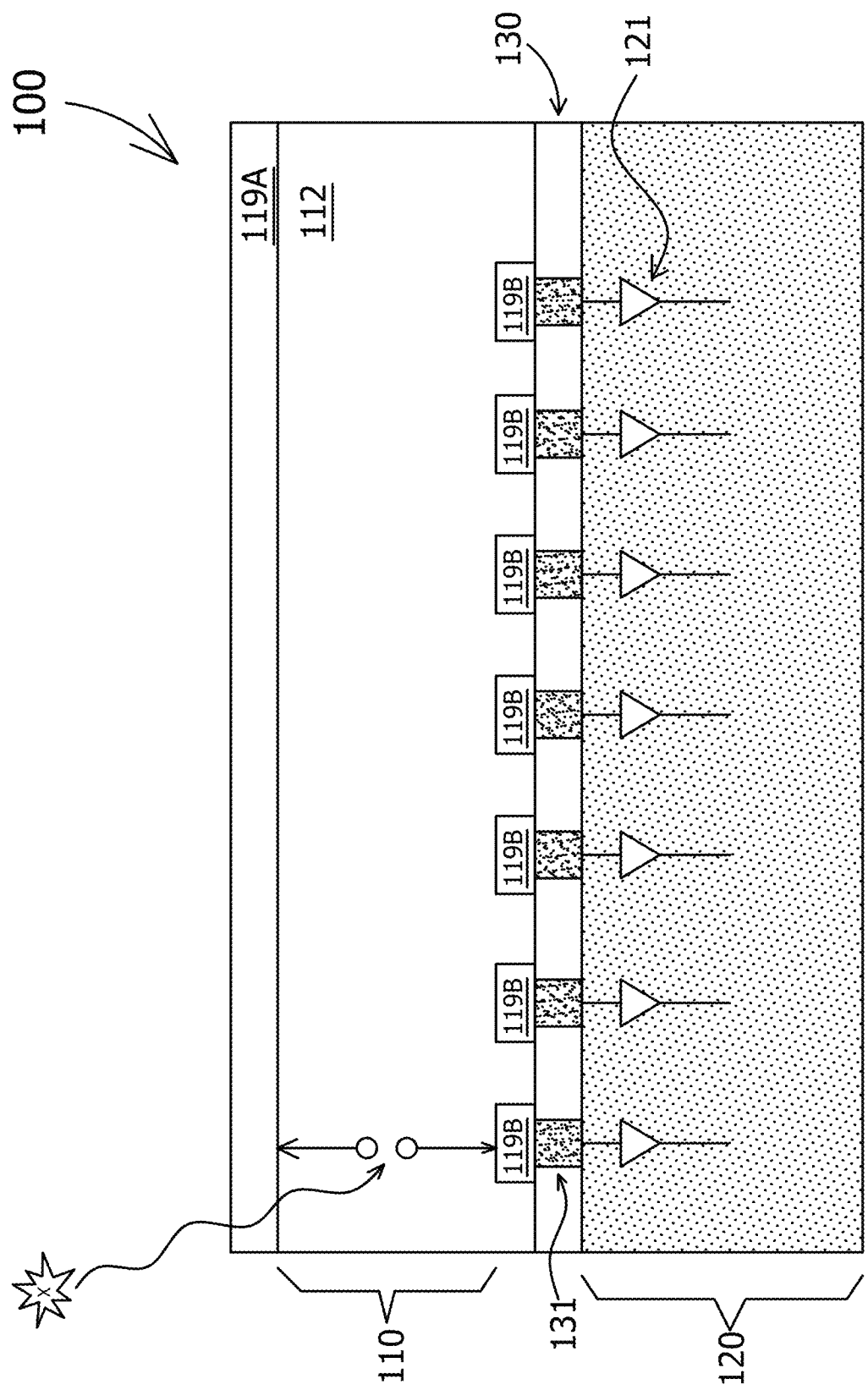
FIG. 2C schematically shows an alternative detailed cross-sectional view of the radiation detector.

FIG. 2C schematically shows an alternative detailed cross-sectional view of the radiation detector 100 of FIG. 1 along the line 2A-2A, according to an embodiment. More specifically, the radiation absorption layer 110 may include a resistor of a semiconductor material such as, silicon, germanium, GaAs, CdTe, CdZnTe, or a combination thereof, but does not include a diode. The semiconductor material may have a high mass attenuation coefficient for the radiation of interest. In an embodiment, the electronics layer 120 of FIG. 2C is similar to the electronics layer 120 of FIG. 2B in terms of structure and function.

When the radiation hits the radiation absorption layer 110 including the resistor but not diodes, it may be absorbed and generate one or more charge carriers by a number of mechanisms. A particle of the radiation may generate 10 to 100,000 charge carriers. The charge carriers may drift to the electrical contacts 119A and 119B under an electric field. The electric field may be an external electric field. The electrical contact 119B includes discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

FIG. 3 schematically shows a top view of a package 200 including the radiation detector 100 and a printed circuit board (PCB) 400. The term "PCB" as used herein is not limited to a particular material. For example, a PCB may include a semiconductor. The radiation detector 100 may be mounted to the PCB 400. The wiring between the detector 100 and the PCB 400 is not shown for the sake of clarity. The PCB 400 may have one or more radiation detectors 100. The PCB 400 may have an area 405 not covered by the radiation detector 100 (e.g., for accommodating bonding wires 410). The radiation detector 100 may have an active area 190, which is where the pixels 150 (FIG. 1) are located. The radiation detector 100 may have a perimeter zone 195 near the edges of the radiation detector 100. The perimeter zone 195 has no pixels and the radiation detector 100 does not detect particles of radiation incident on the perimeter zone 195.

FIG. 4 schematically shows a cross-sectional view of an image sensor 490, according to an embodiment. The image sensor 490 may include a plurality of the packages 200 of FIG. 3 mounted to a system PCB 450. FIG. 4 shows only 2 packages 200 as an example. The electrical connection between the PCBs 400 and the system PCB 450 may be made by bonding wires 410. In order to accommodate the bonding wires 410 on the PCB 400, the PCB 400 may have the area 405 not covered by the detector 100. In order to accommodate the bonding wires 410 on the system PCB 450, the packages 200 may have gaps in between. The gaps may be approximately 1 mm or more. Particles of radiation incident on the perimeter zones 195, on the area 405 or on the gaps cannot be detected by the packages 200 on the system PCB 450. A dead zone of a radiation detector (e.g., the radiation detector 100) is the area of the radiation-receiving surface of the radiation detector, in which incident particles of radiation cannot be detected by the radiation detector. A dead zone of a package (e.g., package 200) is the area of the radiation-receiving surface of the package, in which incident particles of radiation cannot be detected by the detector or detectors in the package. In this example shown in FIG. 3 and FIG. 4, the dead zone of the package 200 includes the perimeter zones 195 and the area 405. A dead zone (e.g., 488) of an image sensor (e.g., image sensor 490) with a group of packages (e.g., packages mounted on the same PCB, packages arranged in the same layer) includes the combination of the dead zones of the packages in the group and the gaps among the packages.

The image sensor 490 including the radiation detectors 100 may have the dead zone 488 incapable of detecting incident radiation. However, the image sensor 490 may capture images of all points of an object (not shown), and then these captured images may be stitched to form a full image of the entire object.

FIG. 5A schematically shows a perspective view of an imaging system 500, according to an embodiment. In an embodiment, the imaging system 500 may comprise a radiation source system 510+520 and the image sensor 490.

For simplicity, only one radiation detector 100 of the image sensor 490 is shown. In an embodiment, the radiation source system 510+520 may comprise a radiation source 510 and a filter 520. In an embodiment, the filter 520 may comprise a pinhole 522. The pinhole 522 may have the shape of a circle, a rectangle, a square, etc. In an embodiment, the filter 520 may comprise a silicon substrate (not shown) with a metal layer (not shown) on a surface of the substrate. The metal layer may have an aperture that plays the role of the pinhole 522. The silicon substrate does not necessarily have a physical hole.

For simplicity, only the active area 190 of the radiation detector 100 is shown in FIG. 5A (i.e., the other parts of the radiation detector 100 are not shown). In an embodiment, an object 530 may be positioned between the radiation source system 510+520 and the radiation detector 100.

In an embodiment, the operation of the imaging system 500 may be carried out in multiple exposures as follows. During a first exposure, a pencil radiation beam 513a may be sent from the pinhole 522 of the filter 520 and aimed at a target region 513at on the active area 190. A radiation beam is said to be aimed at a region or point if the entire region or point would be exposed to the radiation beam in vacuum (i.e., without the presence of the object 530). In this case, it is also said that the region or point is targeted by the radiation beam, or the radiation beam targets the region or point. Assume that the pencil radiation beam 513a intersects the object 530 and then is incident on an incident region 513ai on the active area 190.

In an embodiment, during the first exposure, the radiation detector 100 may capture an image of the pencil radiation beam 513a. Next, in an embodiment, the radiation detector 100 may determine the position of the incident region 513ai based on the captured image of the pencil radiation beam 513a. Next, in an embodiment, the radiation detector 100 may determine an offset 513ax between the incident region 513ai and the target region 513at based on the determined position of the incident region 513ai.

In an embodiment, the pencil radiation beam 513a may be created by sending a cone radiation beam 513.1 from the radiation source 510 toward the pinhole 522 of the filter 520. In an embodiment, only the portion of the cone radiation beam 513.1 incident on the pinhole 522 may be allowed to pass the filter 520 thereby resulting in the pencil radiation beam 513a.

Figure 5B:
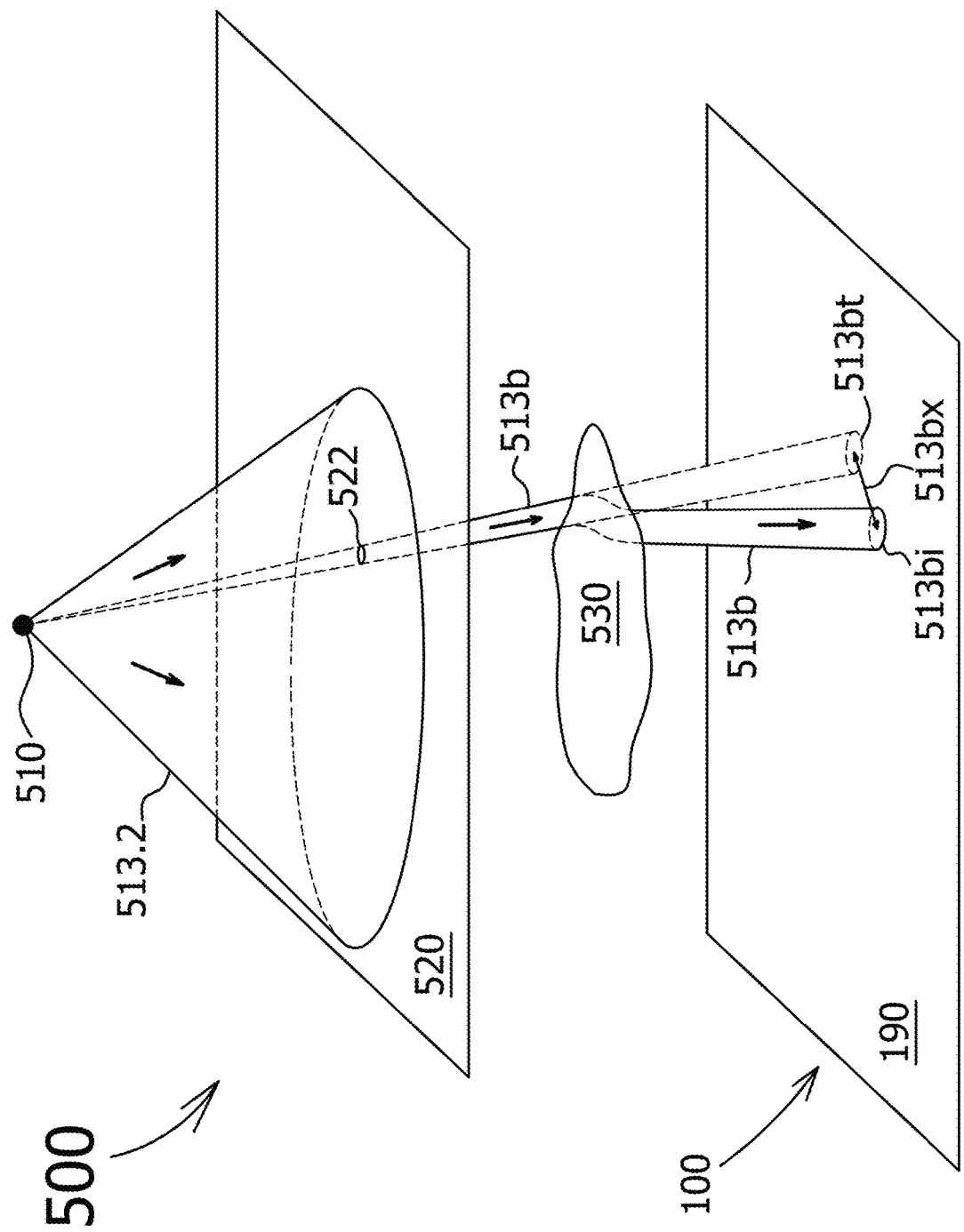

Next, during a second exposure, in an embodiment, with reference to FIG. 5B, a pencil radiation beam 513b may be sent from the pinhole 522 of the filter 520 and aimed at a target region 513bt on the active area 190. Assume that the pencil radiation beam 513b intersects the object 530 and then is incident on an incident region 513bi on the active area 190. The words "first", "second", and other ordinal numerals in this disclosure are used only for easy reference and do not imply any chronological order or any place of occurrence. For example, just by the use of "first" and "second", there is no implication that the second exposure is performed after the first exposure is performed. For another example, just by the use of "first" and "second", there is no implication that the first exposure and the second exposure are performed in the same imaging system (e.g., the imaging system 500).

In an embodiment, during the second exposure, the radiation detector 100 may capture an image of the pencil radiation beam 513b. Next, in an embodiment, the radiation detector 100 may determine the position of the incident region 513bi based on the captured image of the pencil radiation beam 513b. Next, in an embodiment, the radiation detector 100 may determine an offset 513bx between the incident region 513bi and the target region 513bt based on the determined position of the incident region 513bi.

In an embodiment, the pencil radiation beam 513b may be created as follows. After the first exposure is performed and before the second exposure is performed (i.e., between the first and second exposures), the filter 520 may be moved relative to the radiation detector 100, the radiation source 510, and the object 530 (while the radiation detector 100, the radiation source 510, and the object 530 are stationary with respect to each other) from the position as shown in FIG. 5A to another position as shown in FIG. 5B (i.e., to the right). Then, in an embodiment, during the second exposure, a cone radiation beam 513.2 may be sent from the radiation source 510 toward the pinhole 522 of the filter 520 thereby creating the pencil radiation beam 513b.

Next, in an embodiment, after the second exposure is performed, additional exposures similar to the first and second exposures may be performed. Specifically, additional pencil radiation beams (similar to the pencil radiation beams 513a and 513b) may be sent from the pinhole 522 during the additional exposures. The filter 520 may be moved relative to the radiation detector 100 between the additional exposures. The associated offsets (similar to the offsets 513ax and 513bx) may be determined in a similar manner.

Each of the pencil radiation beams mentioned above may either intersect or miss the object 530. The case in which the pencil radiation beam intersects the object 530 is described above (e.g., the case of the pencil radiation beam 513a described with reference to FIG. 5A). If the pencil radiation beam misses the object 530, then the associated offset would be determined to be zero (because the associated incident region is the same as the associated target region).

FIG. 5C shows a flowchart 580 generalizing and summarizing an operation of the imaging system 500, according to an embodiment. In step 582, in an embodiment, for i=1, . . . , M, a pencil radiation beam (i) may be sent incident on an incident region (i) on the active area 190 of the radiation detector 100, wherein the pencil radiation beam (i) is aimed at a target region (i) on the active area 190, and wherein M is a positive integer. For example, with reference to FIG. 5A, the pencil radiation beam 513a may be sent incident on the incident region 513ai on the active area 190 of the radiation detector 100, wherein the pencil radiation beam 513a may be aimed at the target region 513at on the active area 190.

In step 584, in an embodiment, for i=1, . . . , M, an offset (i) between the incident region (i) and the target region (i) may be determined. For example, with reference to FIG. 5A, the offset 513ax between the incident region 513ai and the target region 513at may be determined.

In summary, for any target region on the active area 190, the position of the associated incident region is determined in terms of the offset between the incident region and the target region. For example, in FIG. 5A, for the target region 513at, the position of the associated incident region 513ai is determined in terms of the offset 513ax. Similarly, in FIG. 5B, for the target region 513bt, the position of the associated incident region 513bi is determined in terms of the offset 513bx.

In an embodiment, the pencil radiation beams (i), i=1, . . . , M may be X-ray beams. In an embodiment, each point of the object 530 may be targeted by at least a pencil radiation beam of the pencil radiation beams (i), i=1, . . . , M. In other words, the pencil radiation beams (i), i=1, . . . , M scan the entire object 530.

In an embodiment, in the case where the entire object 530 is scanned by the pencil radiation beams (i), i=1, . . . , M as mentioned above, the radiation detector 100 may determine a refractive index for each point of the object 530 based on all the determined offsets (i), i=1, . . . , M. In an embodiment, the size of each of the target regions (i), i=1, . . . , M may be at least the size of a pixel 150 of the radiation detector 100.

In the embodiments described above, with reference to FIG. 5A & FIG. 5B, only one pencil radiation beam is sent during each exposure. For example, only the pencil radiation beam 513a is sent during the first exposure. Similarly, only the pencil radiation beam 513b is sent during the second exposure. In an alternative embodiment, the pencil radiation beams (e.g., both the pencil radiation beam 513a and the pencil radiation beam 513b) may be simultaneously sent from the filter 520 during the first exposure as shown in FIG. 5D.

In an embodiment, during the first exposure, the radiation detector 100 may capture an image of both the pencil radiation beams 513a and 513b. Then, in an embodiment, the radiation detector 100 may determine the positions of the incident regions 513ai and 513bi based on the captured image. Then, in an embodiment, the radiation detector 100 may determine the offsets 513ax and 513bx based on the determined positions of the incident regions 513ai and 513bi.

In an embodiment, during the first exposure, the pencil radiation beam 513a and the pencil radiation beam 513b may be simultaneously created by sending the cone radiation beam 513.1 from the radiation source 510 toward two pinholes 522 and 522' of the filter 520 (i.e., the filter 520 may have the additional pinhole 522' in addition to the pinhole 522). In an embodiment, only the portions of the cone radiation beam 513.1 incident on the pinholes 522 and 522' may be allowed to pass the filter 520 thereby resulting in the pencil radiation beams 513a and 513b, respectively.

In general, the filter 520 may have one pinhole or multiple pinholes (similar to the pinhole 522). The more pinholes the filter 520 has, the more resulting pencil radiation beams (similar to the pencil radiation beam 513a) may be sent simultaneously from the filter 520 during each exposure, and therefore the faster the object 530 may be scanned with the resulting pencil radiation beams.

In an embodiment, with reference to the flowchart 580 of FIG. 5C, images of the pencil radiation beams (i), i=1, . . . , M may be captured using the radiation detector 100. In an embodiment, said determining the offset (i) of step 584 may comprise (A) determining a position (i) of the incident region (i) based on the captured image of the pencil radiation beam (i), and (B) determining the offset (i) based on the position (i) of the incident region (i).

For example, with reference to FIG. 5A, the offset 513ax may be determined by (A) determining the position of the incident region 513ai based on the captured image of the pencil radiation beam 513, and (B) determining the offset 513ax based on the position of the incident region 513ai.

In an embodiment, with reference to FIG. 5D, the minimum distance 513d between the target region 513at and the target region 513bt may be at least a pre-specified distance so as to avoid confusion as to which pencil radiation beam is incident on which incident region. In an embodiment, in general, with the filter 520 having multiple pinholes, a minimum distance between any two points of any two target regions on the active area 190 of any two beams (A) being of the pencil radiation beams (i), i=1, . . . , M and (B) being sent during any one exposure in the imaging system 500 may be at least a pre-specified distance.

In an embodiment, the pre-specified distance may be in terms of an absolute length unit (e.g., in microns). In an alternative embodiment, the pre-specified distance may be in terms of the size of a pixel 150 of the radiation detector 100. For example, the pre-specified distance may be 10 times the size of a pixel 150.

In an embodiment, improvements may be made in determining the position of an incident region (e.g., the incident region 513ai of FIG. 5A), especially when the size of the incident region is smaller than the size of the pixel 150 of the radiation detector 100. Specifically, with reference to FIG. 5A, for the pencil radiation beam 513a, additional pencil radiation beams (not shown) may be sent one after another incident on the active area 190 wherein each of the additional pencil radiation beams is parallel to and overlaps the pencil radiation beam 513a. In an embodiment, these additional pencil radiation beams may be created by moving the filter 520 relative to the radiation detector 100 by small displacements and sending different cone radiation beams (similar to the cone radiation beam 513.1) from the radiation source 510 toward the pinhole 522. In an embodiment, these additional pencil radiation beams may be created by moving the radiation detector 100 relative to the filter 520 by small displacements. Then, in an embodiment, a super resolution algorithm may be applied to images (captured by the radiation detector 100) of the pencil radiation beam 513a and the additional pencil radiation beams thereby resulting in an enhanced image of the pencil radiation beam 513a. Then, in an embodiment, the position of the incident region 513ai may be determined based on the enhanced image of the pencil radiation beam 513a. Then, in an embodiment, the offset 513ax may be determined based on the determined position of the incident region 513ai.

In general, with reference to FIG. 5A-FIG. 5D, in an embodiment, for i=1, . . . , M, additional pencil radiation beams (i, j), j=1, . . . , Ni, wherein Ni is a positive integer, wherein each additional pencil radiation beam of the additional pencil radiation beams (i, j), j=1, . . . , Ni is parallel to and overlaps the pencil radiation beam (i). In an embodiment, images of the pencil radiation beams (i), i=1, . . . , M and the additional pencil radiation beams (i, j), i=1, . . . , M, and j=1, . . . , Ni may be captured using the radiation detector 100.

In an embodiment, for i=1, . . . , M, a super resolution algorithm may be applied to the image of the pencil radiation beam (i) and the images of the additional pencil radiation beams (i, j), j=1, . . . , Ni thereby resulting in an enhanced image (i) of the pencil radiation beam (i). In an embodiment, said determining the offset (i) comprises (A) determining a position (i) of the incident region (i) based on the enhanced image (i), and (B) determining the offset (i) based on the position (i) of the incident region (i).

Figure 6A:
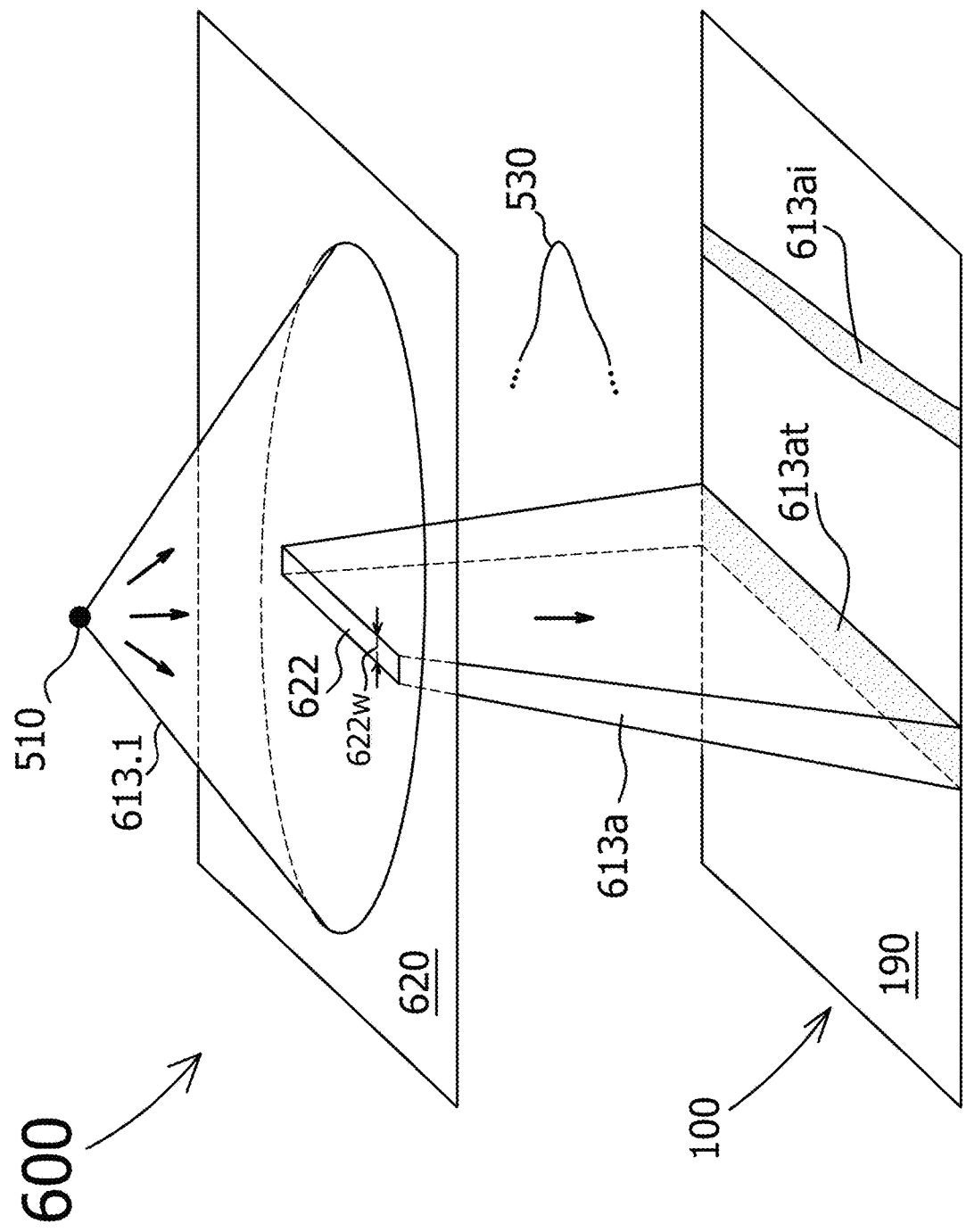

FIG. 6A schematically shows a perspective view of an imaging system 600, according to an embodiment. In an embodiment, the imaging system 600 may be similar to the imaging system 500 of FIG. 5A, except that in the imaging system 600, a filter 620 is used in place of the filter 520. In an embodiment, the filter 620 may comprise a slit 622. In an embodiment, the slit 622 may be similar to the pinhole 522 (FIG. 5A) in structure and function except for the shape.

In an embodiment, the operation of the imaging system 600 may be carried out in multiple exposures as follows.

During a third exposure, a fan radiation beam 613a may be sent from the slit 622 of the filter 620 and aimed at a target region 613at on the active area 190. Assume that the fan radiation beam 613a intersects the object 530 (which is partially shown for simplicity) and then is incident on an incident region 613*ai* on the active area 190. In an embodiment, during the third exposure, the radiation detector 100 may capture an image of the fan radiation beam 613*a*.

In an embodiment, the fan radiation beam 613*a* may be created by sending a cone radiation beam 613.1 from the radiation source 510 toward the slit 622 of the filter 620. In an embodiment, only the portion of the cone radiation beam 613.1 incident on the slit 622 may be allowed to pass the filter 620 thereby resulting in the fan radiation beam 613*a*. In an embodiment, the entire target region 613*at* may be on the active area 190 as shown in FIG. 6A.

Figure 6B:
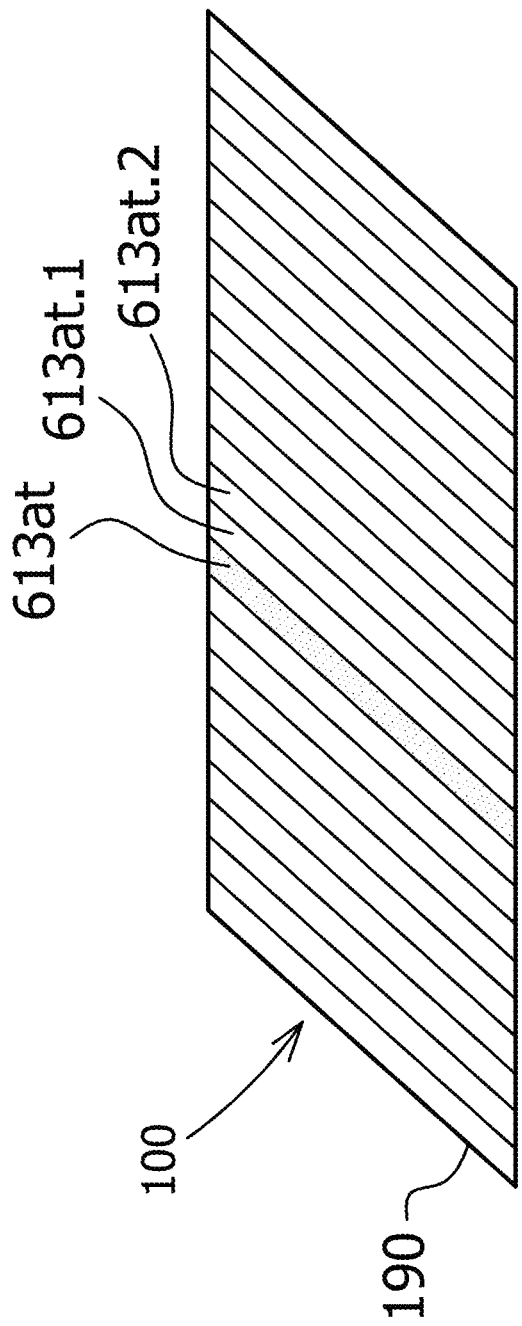

In an embodiment, with reference to FIG. 6B, after the third exposure is performed, first additional exposures similar to the third exposure may be performed one after another. In an embodiment, the target regions associated with the third exposure and the first additional exposures may cover the entire active area 190 as shown in FIG. 6B. In an embodiment, the target regions associated with the third exposure and the first additional exposures may be parallel to each other as shown in FIG. 6B.

For example, with reference to FIG. 6A and FIG. 6B, after the third exposure is performed, the filter 620 may be shifted to the right (i.e., in a direction perpendicular to the slit 622) relative to the radiation detector 100 and the object 530 by a distance equal to the width 622*w* of the slit 622, and then one of the first additional exposures may be performed. The associated target region is region 613*at*.1 as shown in FIG. 6B. After that, for example, the filter 620 may be shifted further to the right relative to the radiation detector 100 by a distance equal to the width 622*w* of the slit 622, and then the next of the first additional exposures may be performed. The associated target region is region 613*at*.2 as shown in FIG. 6B.

Next, in an embodiment, with reference to FIG. 6C, after the first additional exposures are performed, during a fourth exposure, a fan radiation beam 613*b* may be sent from the slit 622 and aimed at a target region 613*bt* on the active area 190. Assume that the fan radiation beam 613*b* intersects the object 530 (which is partially shown for simplicity) and then is incident on an incident region 613*bi* on the active area 190. In an embodiment, during the fourth exposure, the radiation detector 100 may capture an image of the fan radiation beam 613*b*.

In an embodiment, the fan radiation beam 613*b* may be created as follows. After the first additional exposures are performed, the filter 620 may be rotated relative to the radiation detector 100 such that the slit 622 rotates relative to the radiation detector 100 around an axis perpendicular to the filter 620. In an embodiment, the angle of rotation may be greater than 0° and smaller than 180°. In an embodiment, the angle of rotation may be 90° as shown. Then, the fourth exposure may be performed.

In an embodiment, during the fourth exposure, a cone radiation beam 613.2 may be sent from the radiation source 510 toward the slit 622 of the filter 620. In an embodiment, only the portion of the cone radiation beam 613.2 incident on the slit 622 may be allowed to pass the filter 620 thereby resulting in the fan radiation beam 613*b*.

Figure 6D:
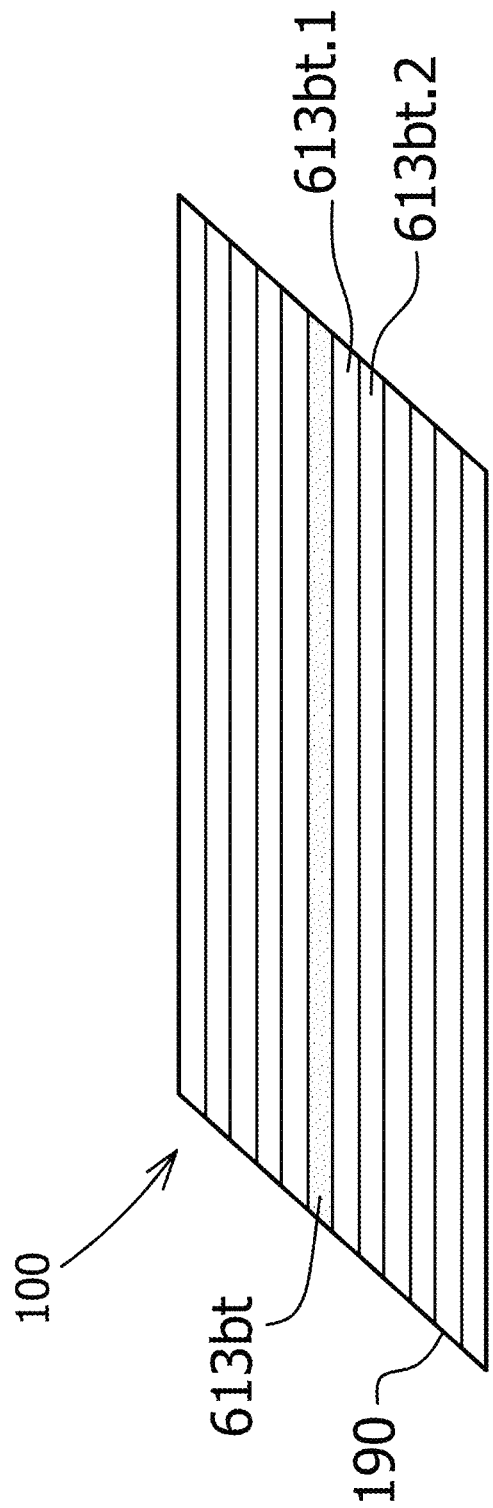

In an embodiment, with reference to FIG. 6D, after the fourth exposure is performed, second additional exposures similar to the fourth exposure may be performed one after another. In an embodiment, the target regions associated with the fourth exposure and the second additional exposures may cover the entire active area 190 as shown in FIG. 6D. In an embodiment, the target regions associated with the fourth exposure and the second additional exposures may be parallel to each other as shown in FIG. 6D.

For example, with reference to FIG. 6C and FIG. 6D, after the fourth exposure is performed, the filter 620 may be shifted toward viewer (i.e., in a direction perpendicular to the slit 622) relative to the radiation detector 100 and the object 530 by a distance equal to the width 622*w* of the slit 622, and then one of the second additional exposures may be performed. The associated target region is region 613*bt*.1 as shown in FIG. 6D. After that, for example, the filter 620 may be shifted further toward viewer relative to the radiation detector 100 by a distance equal to the width 622*w* of the slit 622, and then the next of the second additional exposures may be performed. The associated target region is region 613*bt*.2 as shown in FIG. 6D.

In an embodiment, after the second additional exposures are performed, common target regions each of which is a common region of (A) a target region associated with the third exposure and the first additional exposures (i.e., a target region of FIG. 6B) and (B) a target region associated with the fourth exposure and the second additional exposures (i.e., a target region of FIG. 6D) may be identified, and offsets associated with the identified common target regions may be determined. For example, with reference to FIG. 6E, the radiation detector 100 may identify a common target region 613*ct* which is a common region of (A) the target region 613*at* of the third exposure and (B) the target region 613*bt* of the fourth exposure.

Then, an offset 613*cx* associated with the identified common target region 613*ct* may be determined as follows. First, in an embodiment, the radiation detector 100 may determine the position of a common incident region 613*ci* (which is a common region of (A) the incident region 613*ai* of the fan radiation beam 613*a* and (B) the incident region 613*bi* of the fan radiation beam 613*b*) based on the image of the fan radiation beam 613*a* and the image of the fan radiation beam 613*b* which the radiation detector 100 captured during the third and fourth exposures respectively. Next, in an embodiment, the radiation detector 100 may determine the offset 613*cx* between the common incident region 613*ci* and the common target region 613*ct* based on the determined position of the common incident region 613*ci*.

FIG. 6F shows a flowchart 680 generalizing and summarizing an operation of the imaging system 600, according to an embodiment. In step 682, in an embodiment, first fan radiation beams (e.g., the fan radiation beams of the third exposure and the first additional exposures whose target regions are shown in FIG. 6B) and second fan radiation beams (e.g., the fan radiation beams of the fourth exposure and the second additional exposures whose target regions are shown in FIG. 6D) may be sent incident on the active area 190 of the radiation detector 100, wherein for i=1, . . . , M, a pair (i) of one of the first fan radiation beams (e.g., the fan radiation beam 613*a*) and one of the second fan radiation beams (e.g., the fan radiation beam 613*b*) are incident on two incident regions (e.g., the 2 incident regions 613*ai* and 613*bi*) on the active area 190, the two incident regions sharing a common incident region (i) (e.g., the common incident region 613*ci*) on the active area 190, wherein M is a positive integer, and wherein for i=1, . . . , M, the pair (i) (e.g., the fan radiation beams 613*a* and 613*b*) are aimed at two target regions (e.g., the 2 target regions 613*at* and 613*bt*) on the active area 190, the two target regions sharing a common target region (i) (e.g., the common target region 613*ct*) on the active area 190.

In step 684, for i=1, . . . , M, an offset (i) between the common incident region (i) and the common target region (i) may be determined. For example, with reference to FIG. 6E, the offset 613cx between the common incident region 613ci and the common target region 613ct may be determined.

In an embodiment, the first and second fan radiation beams used in the imaging system 600 may be X-ray beams. In an embodiment, each point of the object 530 may be targeted by each beam of at least a pair of the pairs (i), i=1, . . . , M. In other words, each point of the object 530 is targeted by (A) at least a beam of the first fan radiation beams, and (B) at least a beam of the second fan radiation beams.

In an embodiment, in the case where each point of the object 530 is targeted by each beam of at least a pair of the pairs (i), i=1, . . . , M, the radiation detector 100 of the imaging system 600 may determine a refractive index for each point of the object 530 based on all the offsets (i), i=1, . . . , M determined in step 684 (FIG. 6F). In an embodiment, the size of each common target region of the common target regions (i), i=1, . . . , M (e.g., the common target region 613ct) is at least the size of a pixel 150 of the radiation detector 100.

In the embodiments described above with reference to FIG. 6A-FIG. 6E, during each exposure, only one fan radiation beam is sent from the filter 620. For example, only the fan radiation beam 613a is sent during the third exposure as shown in FIG. 6A. For another example, only the fan radiation beam 613b is sent during the fourth exposure as shown in FIG. 6C. This is because the filter 620 has only one slit 622.

Figure 7A:
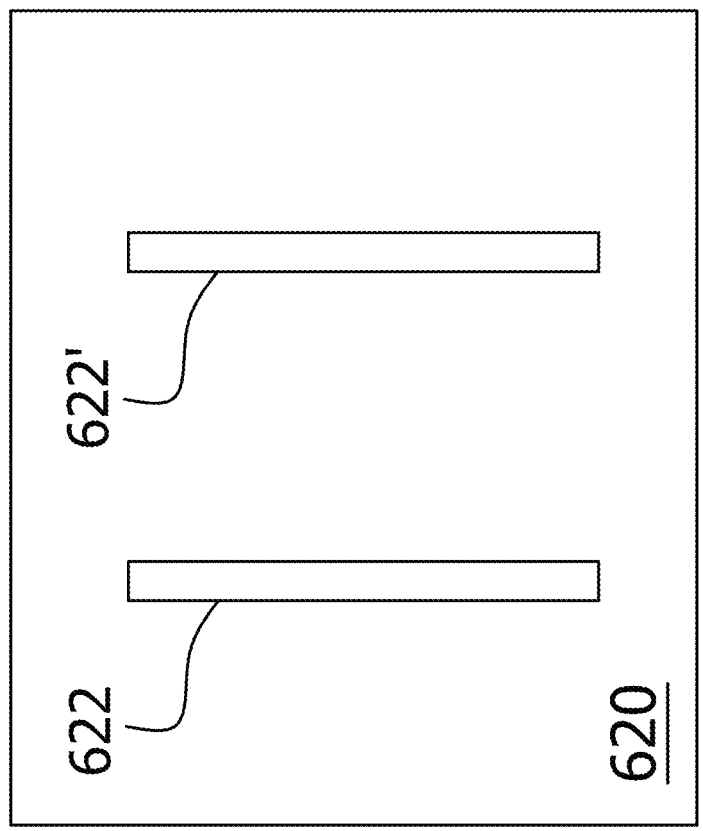
FIG. 7A-FIG. 7G show the operation of the imaging system of FIG. 6A-FIG. 6F with different embodiments of a filter.
Figure 7B:
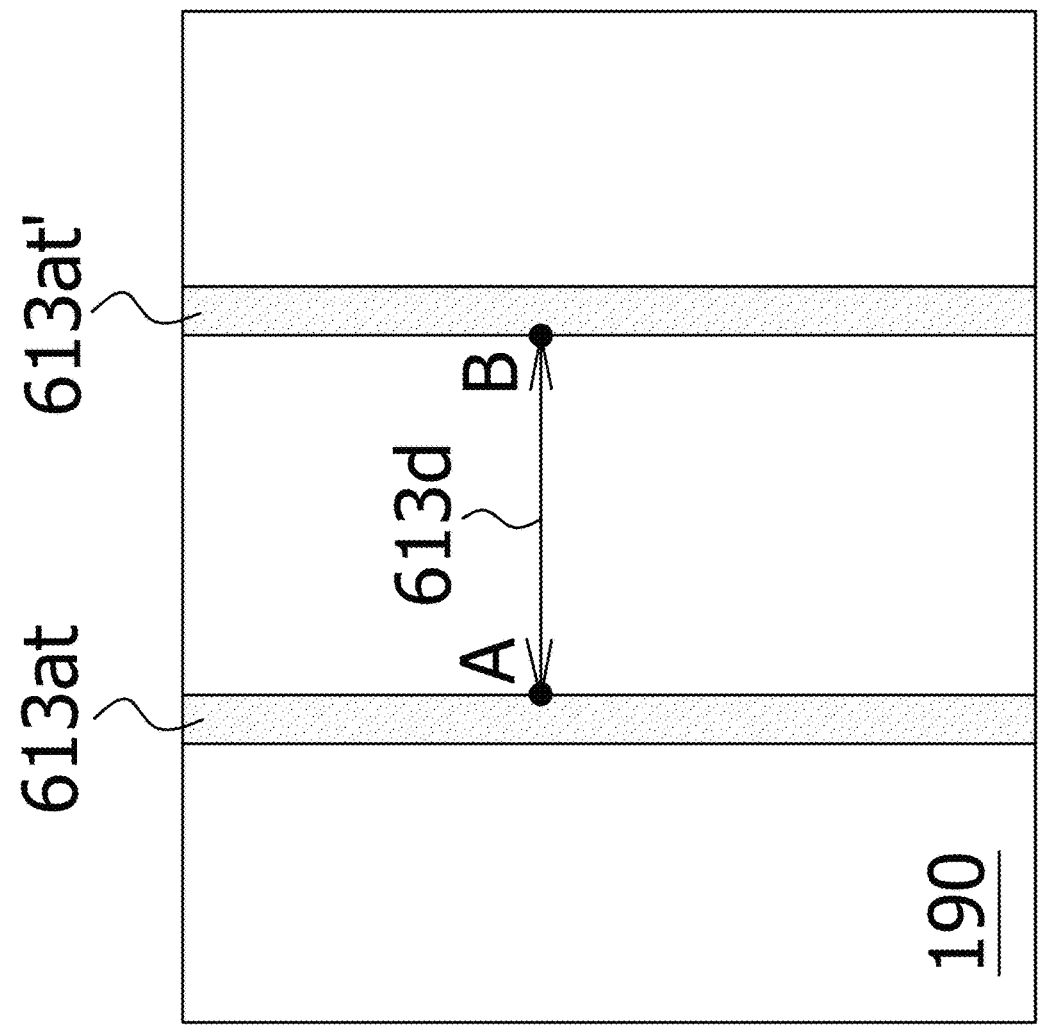

In an alternative embodiment, with reference to FIG. 7A & FIG. 7B, the filter 620 may have an additional slit 622' in addition to the slit 622. As a result, during the third exposure, in an embodiment, two fan radiation beams may be sent simultaneously from the two slits 622 and 622' targeting two target regions 613at and 613at' respectively. Therefore, the scanning of the object 530 by the fan radiation beams as can be seen in the scanning of the active area 190 by the fan radiation beams (FIG. 6B and FIG. 6D) would be twice faster.

In general, the filter 620 may have one slit (e.g., the slit 622) or multiple slits (similar to the slit 622). The more slits the filter 620 has, the more fan radiation beams (similar to the fan radiation beam 613a) may be simultaneously sent from the slits during each exposure in the imaging system 600, and therefore the faster the scanning of the object 530 may progress.

In an embodiment, in case where multiple fan radiation beams are sent simultaneously from the filter 620 during an exposure, to avoid confusion as to which fan radiation beam is incident on which incident region, the minimum distance between any two points of any two target regions on the active area 190 of any two beams (A) being of the first and second fan radiation beams and (B) being sent during any one exposure in the imaging system 600 (e.g., the distance 613d between 2 points A and B of the target regions 613at and 613at' respectively in FIG. 7B) may be at least a pre-specified distance.

In an embodiment, the pre-specified distance may be in terms of an absolute length unit (e.g., microns), or in terms of the size of a pixel 150 of the radiation detector 100. In an embodiment, the pre-specified distance may be 10 times the size of a pixel 150 of the radiation detector 100.

In an embodiment, the two slits 622 and 622' may be parallel to each other as shown in FIG. 7A. As a result, the 2 fan radiation beams (not shown) sent from the 2 slits 622 and 622' during the third exposure are aimed at the two parallel target regions 613at and 613at' as show in FIG. 7B.

In an embodiment, the filter 620 with the 2 parallel slits 622 and 622' may be moved relative to the radiation detector 100 between multiple exposures (e.g., the third exposure, the first additional exposures, the fourth exposure, and the second additional exposures) so that the fan radiation beams from the slits 622 and 622' scan the object 530 twice during the multiple exposures as can be seen in the scanning of the active area 190 twice in FIG. 6B and FIG. 6D.

Figure 7C:
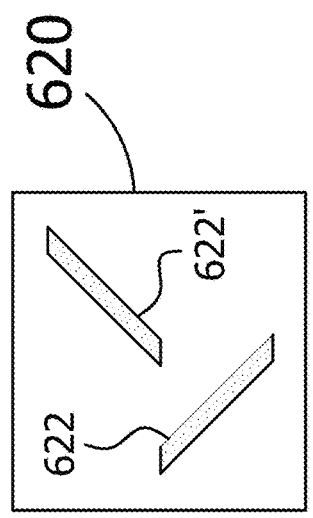
Figure 7D:
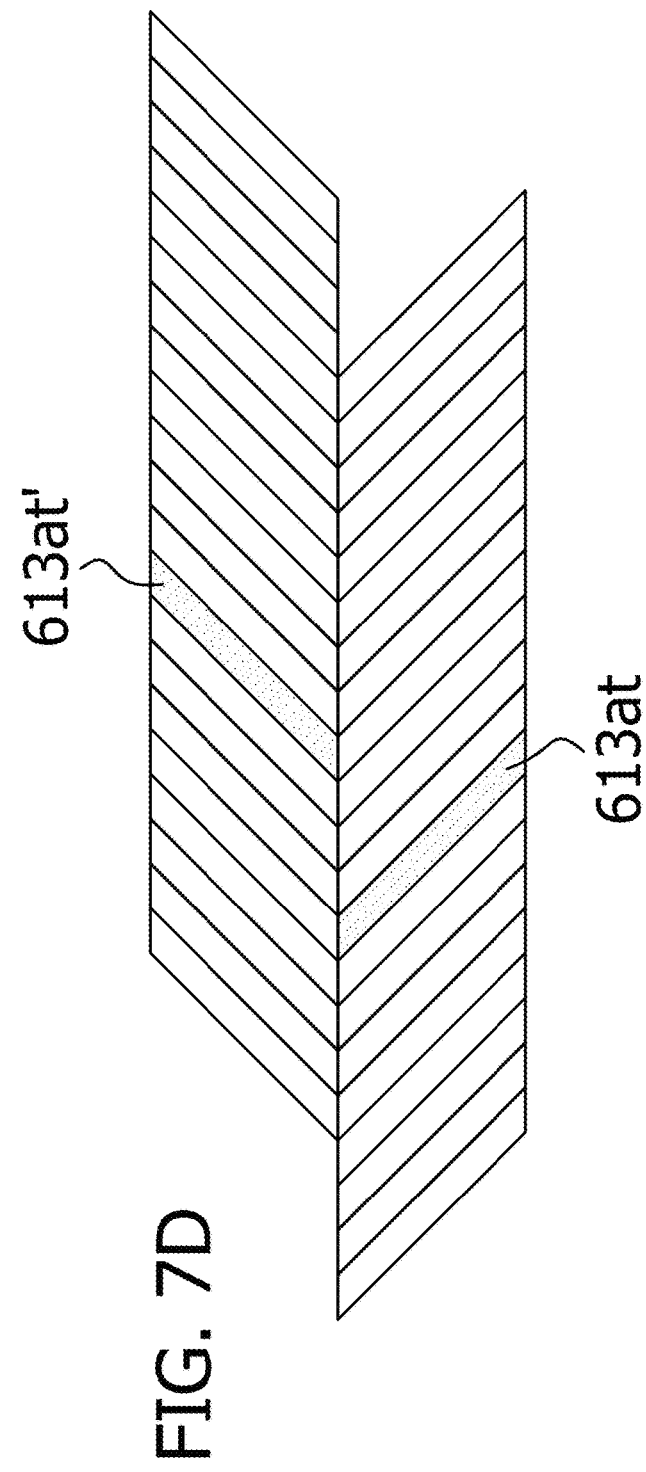
Figure 7E:
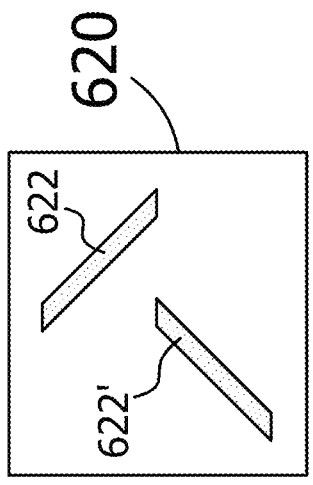

In an alternative embodiment, the two slits 622 and 622' of the filter 620 may be non-parallel to each other as shown in FIG. 7C & FIG. 7E. In an embodiment, the two slits 622 and 622' may be perpendicular to each other. In an embodiment, between exposures, the filter 620 may be shifted relative to the radiation detector 100 in a direction not parallel to any one of the non-parallel slits 622 and 622'.

FIG. 7D shows the two target regions 613at and 613at' and other target regions on an imaginary plane containing the active area 190 (not shown for simplicity) as a result of a first scan of the imaginary plane using fan radiation beams from the 2 non-parallel slits 622 and 622' of FIG. 7C during the third exposure and the first additional exposures, according to an embodiment.

Figure 7F:
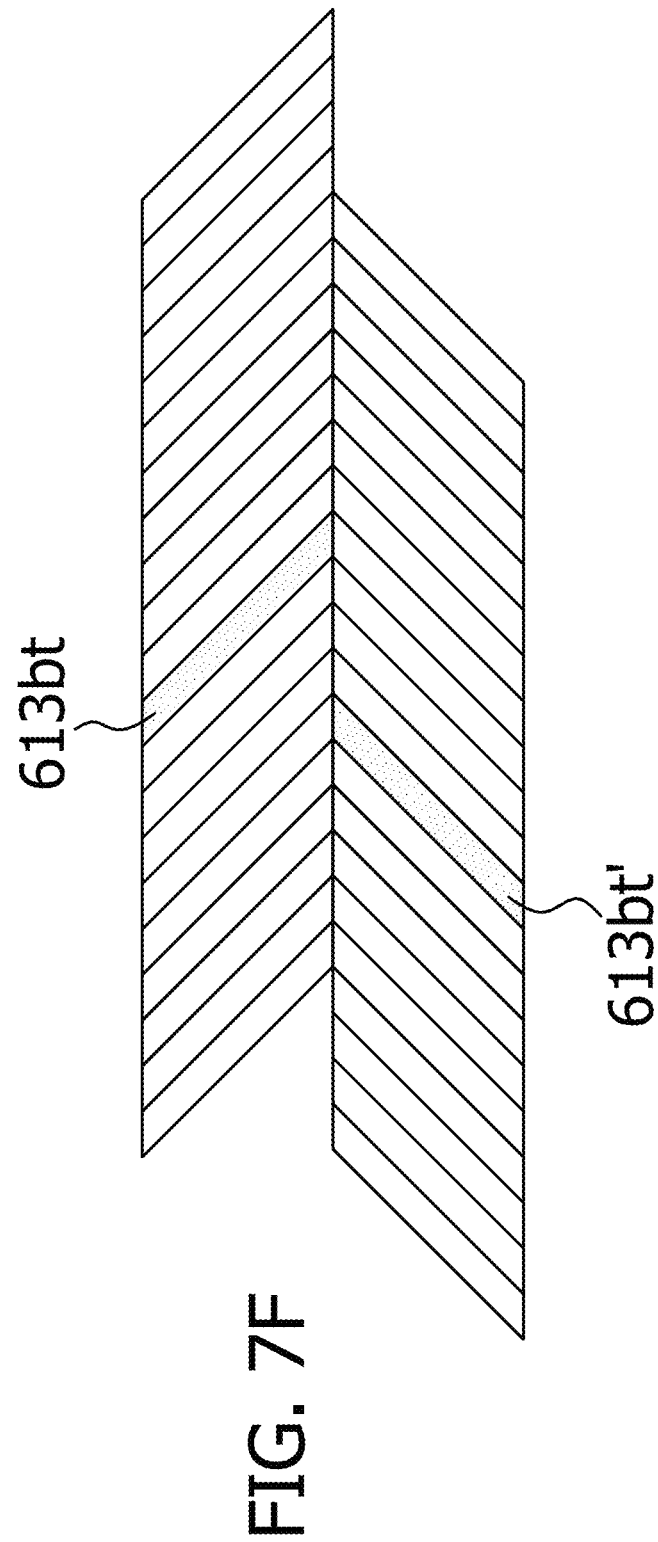

Similarly, FIG. 7F shows the two target regions 613bt and 613bt' and other target regions on the imaginary plane as a result of a second scan of the imaginary plane using fan radiation beams from the 2 non-parallel slits 622 and 622' of FIG. 7E during the fourth exposure and the second additional exposures, according to an embodiment. More specifically, in an embodiment, after the first additional exposures are performed, the filter 620 of FIG. 7C may be rotated 180° resulting in the filter 620 of FIG. 7E. Then, the filter 620 may be used to make the second scan (which may be similar to the first scan in an embodiment) resulting in the target regions as shown in FIG. 7F.

Figure 7G:
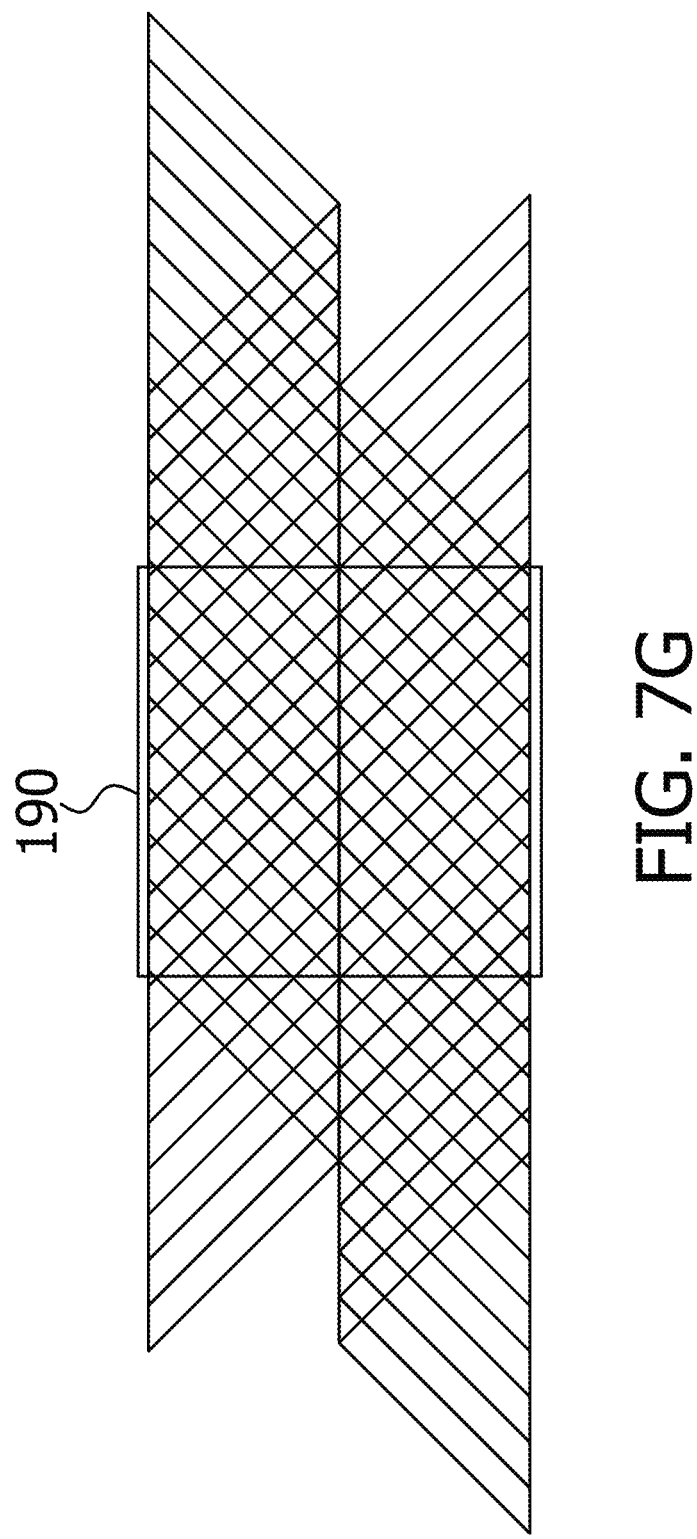

FIG. 7G shows the target regions on the imaginary plane as a result of both the first scan and the second scan of the imaginary plane with the fan radiation beams from the slits 622 and 622'. In an embodiment, each point of the active area 190 may be (A) in at least a target region of the first scan, and (B) in at least a target region of the second scan as shown in FIG. 7G.

In an embodiment, with reference to the flowchart 680 of FIG. 6F, images of the first and second fan radiation beams may be captured using the radiation detector 100. In an embodiment, said determining the offset (i) of step 684 may comprise (A) determining a position (i) of the common incident region (i) based on the two captured images of the two beams of the pair (i), and (B) determining the offset (i) based on the position (i) of the common incident region (i).

Figure 6E:
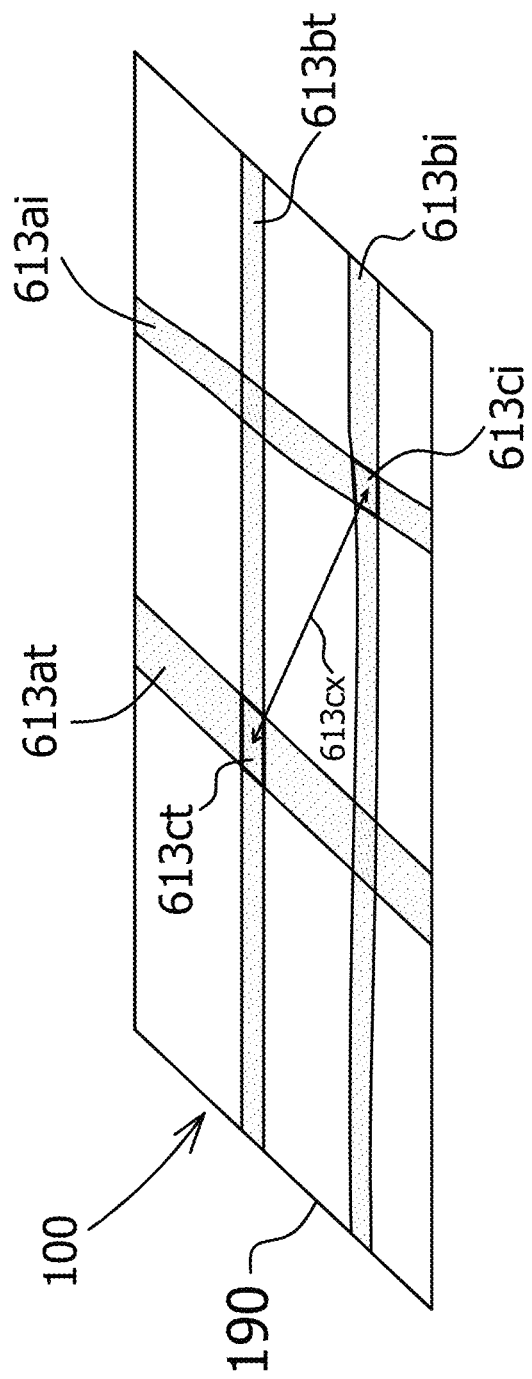

For example, with reference to FIG. 6E, the offset 613cx may be determined by (A) determining the position of the common incident region 613ci based on the 2 captured images of the 2 beams of the corresponding pair of the fan radiation beams 613a and 613b, and (B) determining the offset 613cx based on the position of the common incident region 613ci.

In an embodiment, improvements may be made in determining the position of a common incident region (e.g., the common incident region 613ci of FIG. 6E), especially when the size of the common incident region is smaller than the size of the pixel 150 of the radiation detector 100.

Specifically, with reference to the flowchart 680 of FIG. 6F, in an embodiment, for each beam of the first and second fan radiation beams (e.g., the fan radiation beam 613a of FIG. 6A), additional fan radiation beam(s) may be sent, each of which is parallel to and overlaps said beam (i.e., the beam 613a) of the first and second fan radiation beams. In an embodiment, images of the first and second fan radiation beams and their associated additional fan radiation beams may be captured using the radiation detector 100.

In an embodiment, for each beam of the first and second fan radiation beams (e.g., the fan radiation beam 613a of FIG. 6A), a super resolution algorithm may be applied to the image of said beam (i.e., the beam 613a) and the images of the additional fan radiation beam(s) associated with said beam thereby resulting in an enhanced image of said beam.

In an embodiment, said determining the offset (i) in step 684 may comprise (A) determining a position (i) of the common incident region (i) based on the two enhanced images of the two beams of the pair (i), and (B) determining the offset (i) based on the position (i) of the common incident region (i). For example, with reference to FIG. 6E, said determining the offset 613cx of step 684 may comprise (A) determining the position of the common incident region 613ci based on the two enhanced images of the two beams 613a and 613b, and (B) determining the offset 613cx based on the position of the common incident region 613ci.

In an embodiment, with reference to the flowchart 680 of FIG. 6F, the first fan radiation beams may be parallel to each other (e.g., the fan radiation beam 613a and other fan radiation beams of the third exposure and the first additional exposures as indicated in FIG. 6A-FIG. 6B), and the second fan radiation beams may be parallel to each other (e.g., the fan radiation beam 613b and other fan radiation beams of the fourth exposure and the second additional exposures as indicated in FIG. 6C-FIG. 6D), but the first fan radiation beams and the second fan radiation beams may be not parallel to each other.

In the embodiments described above, with reference to FIG. 5A-FIG. 7G, in the imaging system 500/600, between exposures, the filter 520/620 is moved relative to the radiation detector 100, the radiation source 510, and the object 530, while the radiation detector 100, the radiation source 510, and the object 530 are stationary with respect to each other.

In an alternative embodiment, between the exposures, the filter 520/620 may make the same movements as described in the embodiments above but the radiation detector 100 may also move with the filter 520/620 relative to the object 530 and the radiation source 510 such that the beam(s) from the filter 520/620 target(s) the same target region(s) on the active area 190 during each of the exposures in the imaging system 500/600. The "(s)" at the end of a word means that the word may be with or without the "s".

For example, with reference to FIG. 5A and FIG. 5B, in the imaging system 500, between the first and second exposures, the radiation detector 100 may move with the filter 520 relative to the object 530 such that the target region 513at (targeted by the pencil radiation beam 513a during the first exposure as shown in FIG. 5A) and the target region 513bt (targeted by the pencil radiation beam 513b during the second exposure as shown in FIG. 5B) are at the same position on the active area 190. In other words, during the second exposure, the pencil radiation beam 513b targets the target region 513at. The pencil radiation beams from the pinhole 522 in subsequent exposures also target the target region 513at.

For another example, with reference to FIG. 5D, in the imaging system 500, between exposures, the radiation detector 100 may move with the filter 520 relative to the object 530 such that the 2 pencil radiation beams from the 2 pinholes 522 and 522' target the same 2 target regions (i.e., target regions 513at and 513bt) on the active area 190 during each of the exposures in the imaging system 500.

For yet another example, with reference to FIG. 6A, FIG. 6B, FIG. 6C, and FIG. 6D, in the imaging system 600, between exposures, the radiation detector 100 may move with the filter 620 relative to the object 530 such that the fan radiation beam from the slit 622 targets the same target region (i.e., the target region 613at) on the active area 190 during each of the exposures in the imaging system 600.

For yet another example, with reference to FIG. 7A and FIG. 7B, in the imaging system 600, between exposures, the radiation detector 100 may move with the filter 620 relative to the object 530 such that the 2 fan radiation beams from the 2 slits 622 and 622' target the same 2 target regions (i.e., the target regions 613at and 613at' of FIG. 7B) on the active area 190 during each of the exposures in the imaging system 600.

In the embodiments described above, with reference to FIG. 5A-FIG. 7G, in the imaging system 500/600, the radiation detector 100 moves with the filter 520/620 relative to the object 530 such that the beam(s) from the filter 520/620 target(s) the same target region(s) on the active area 190 during each of the exposures in the imaging system 500/600, wherein the radiation detector 100 has only one active area 190.

In an alternative embodiment, all things (e.g., structure and function) may remain the same as described above except that the image sensor 490 of FIG. 4 may be used in place of the radiation detector 100 in the imaging system 500/600. In an embodiment, the operation of the imaging system 500/600 including the image sensor 490 may be as follows.

In an embodiment, during a starting exposure (i.e., the very first exposure), the target region(s) may be on the active areas 190 of the image sensor 490. Then, between exposures in the imaging system 500/600, the image sensor 490 may move with the filter 520/620 relative to the object 530 such that the beam(s) from the filter 520/620 target(s) the same target region(s) on the active areas 190 of the image sensor 490 during each of the exposures in the imaging system 500/600.

Figure 8B:
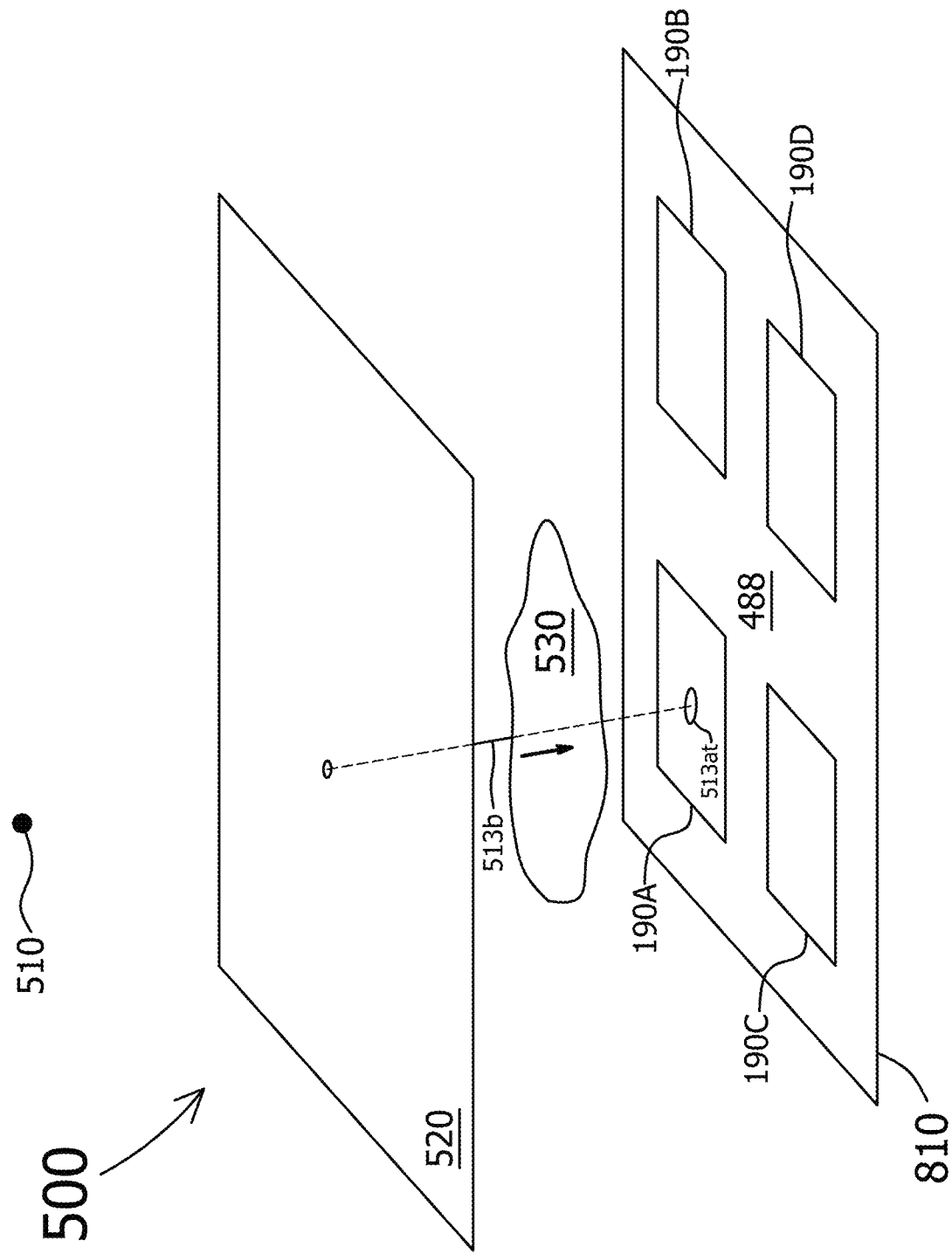

As shown in FIG. 8A, in an embodiment, during a starting exposure, the pencil radiation beam 513a from the pinhole 522 may target the target region 513at on an active area 190A of the image sensor 490 (assuming the image sensor 490 comprises 4 active areas 190A, 190B, 190C, and 190D spatially discontinuous from each other by the dead zone 488 for illustration). After the starting exposure, the image sensor 490 may move with the filter 520 relative to the object 530 such that during the next exposure, the pencil radiation beam 513b from the pinhole 522 targets the same target region (i.e., the target region 513at) on the active area 190A as shown in FIG. 8B.

Figure 8C:
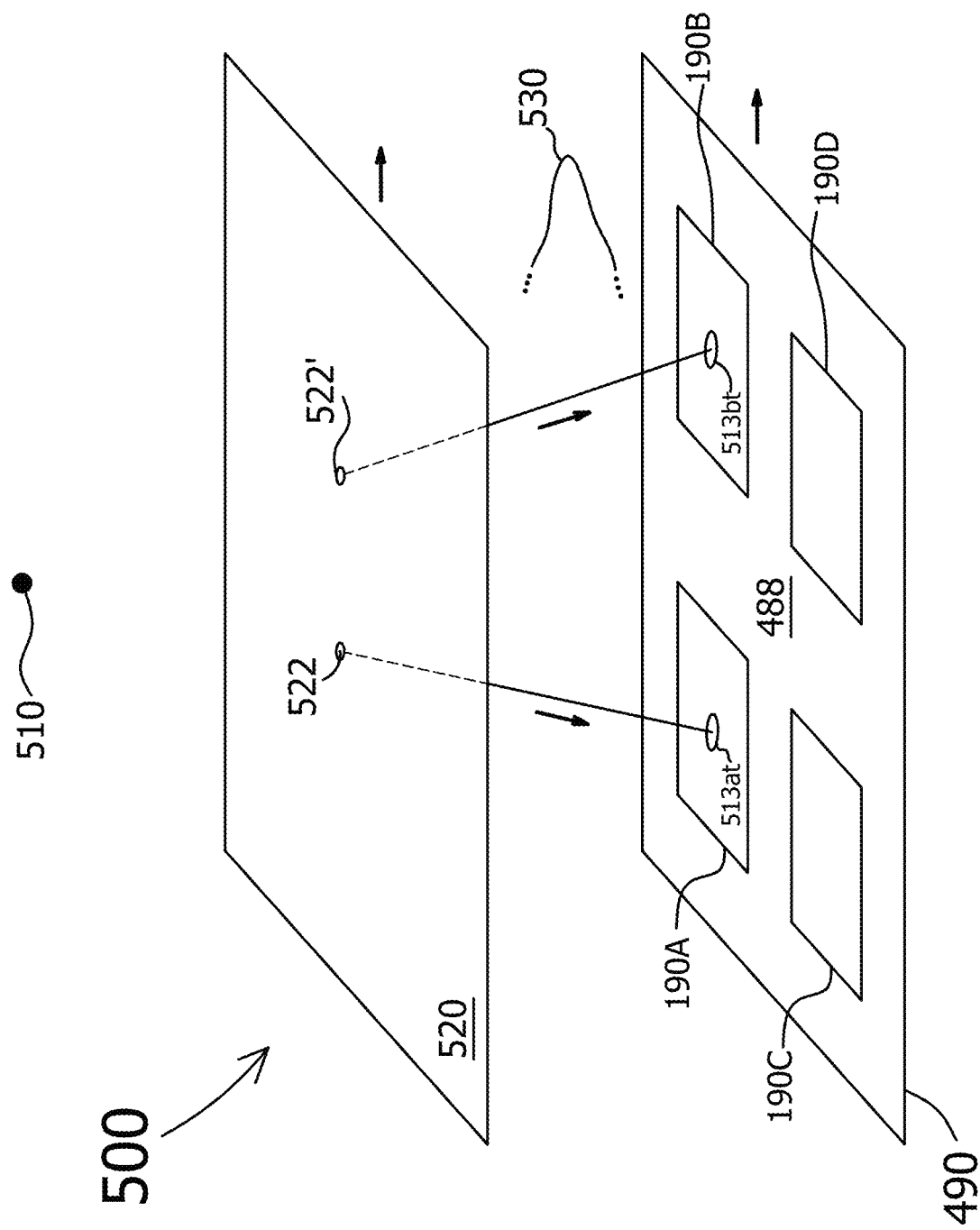

As shown in FIG. 8C, in an embodiment, during a starting exposure, the 2 pencil radiation beams from the pinholes 522 and 522' may target 2 target regions 513at and 513bt on the active areas 190A and 190B of the image sensor 490 as shown.

In an embodiment, after the starting exposure, the image sensor 490 may move with the filter 520 relative to the object 530 such that during the next exposure, the 2 pencil radiation beams from the 2 pinholes 522 and 522' target the same 2 target regions (i.e., the target regions 513at and 513bt) on the active areas 190A and 190B. In an alternative embodiment, both pencil radiation beams from the pinholes 522 and 522' may target 2 target regions 513at and 513bt on a same active area 190 (e.g., the active area 190A) during each of the exposures.

Figure 9A:
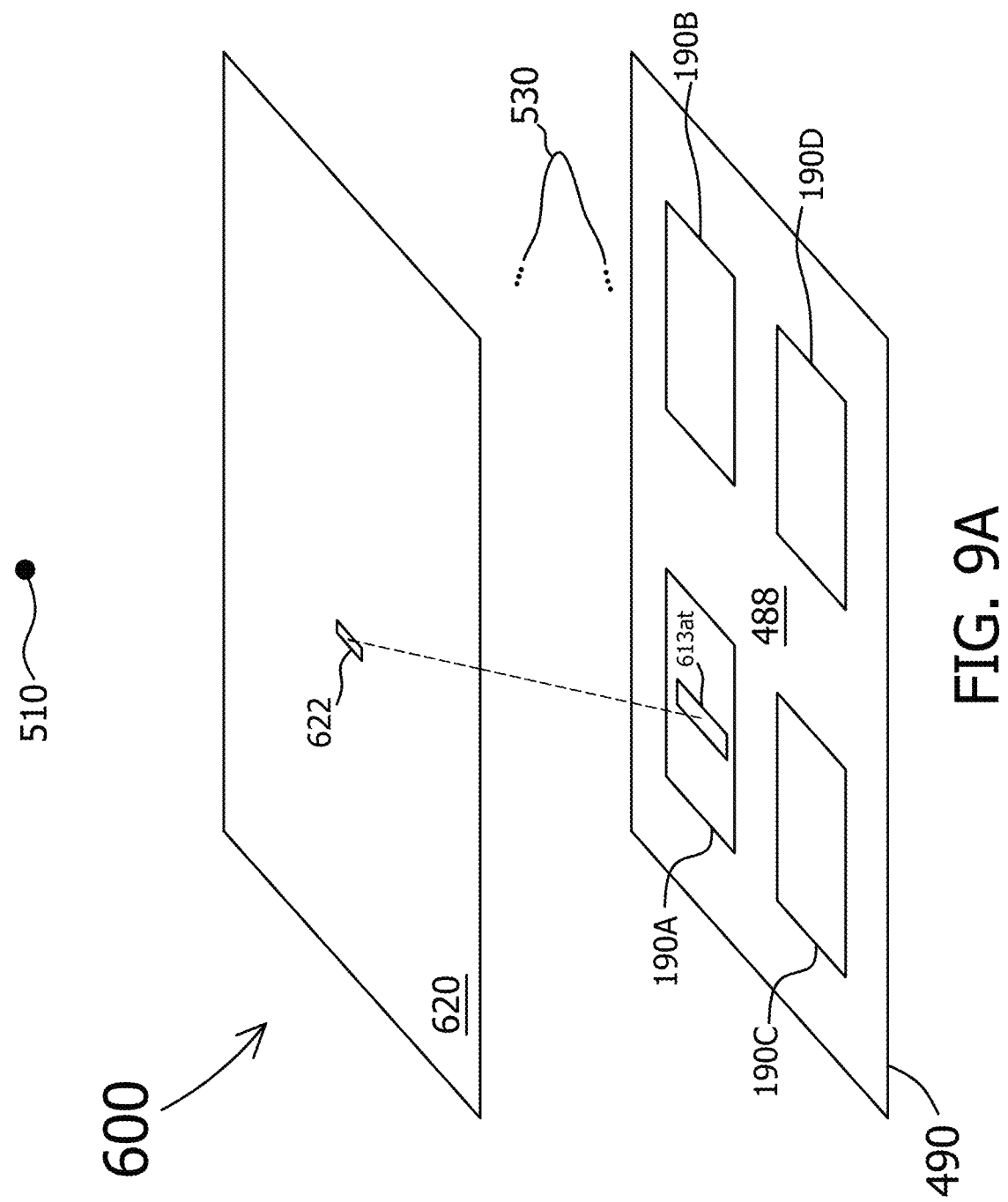
FIG. 9A-FIG. 9C schematically show the imaging system 600 and its operation using the image sensor, according to different embodiments.

As shown in FIG. 9A, in an embodiment, during a starting exposure, the fan radiation beam from the slit 622 may target the target region 613*at* on the active area 190A of the image sensor 490 as shown. In an embodiment, after the starting exposure, the image sensor 490 may move with the filter 620 such that during the next exposure (not shown), the fan radiation beam from the slit 622 targets the same target region (i.e., the target region 613*at*) on the active area 190A.

Figure 9B:
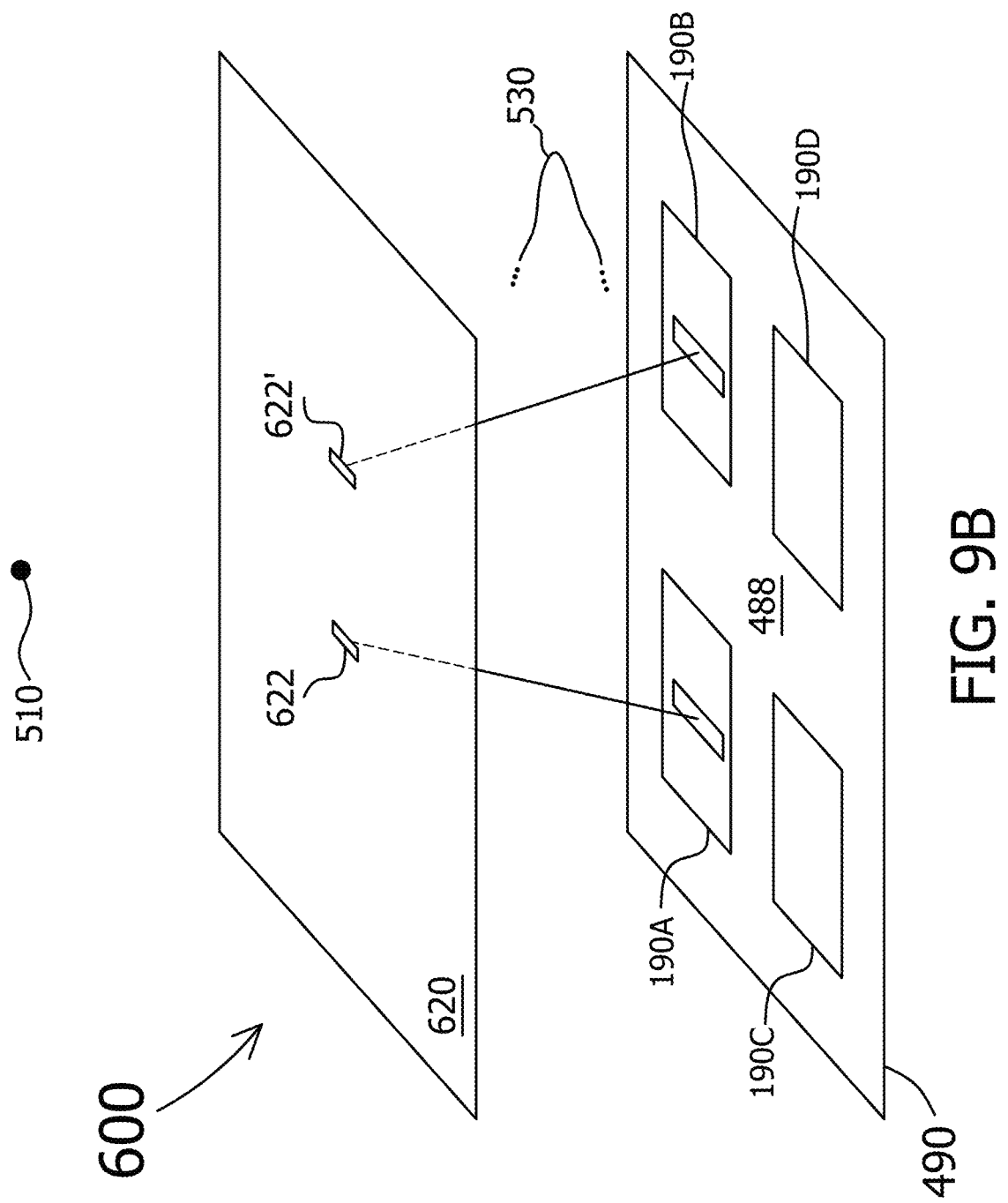

As shown in FIG. 9B, in an embodiment, during a starting exposure, the 2 fan radiation beams from the 2 slits 622 and 622' may target 2 target regions on the active areas 190A and 190B of the image sensor 490 as shown. In an embodiment, after the starting exposure, the image sensor 490 may move with the filter 620 relative to the object 530 such that during the next exposure (not shown), the 2 fan radiation beams from the 2 slits 622 and 622' may target the same 2 target regions on the active areas 190A and 190B.

In an alternative embodiment, with reference to FIG. 9B, during the starting exposure, both fan radiation beams from the 2 slits 622 and 622' may target 2 target regions on a same active area 190 (e.g., the active area 190A). In yet another alternative embodiment (not shown), the filter 620 may comprise 4 parallel slits (similar to the slits 622 and 622'), and during the starting exposure, 4 fan radiation beams from the 4 parallel slits of the filter 620 may target 4 target regions on 4 respective active areas 190A, 190B, 190C, and 190D of the image sensor 490.

Figure 9C:
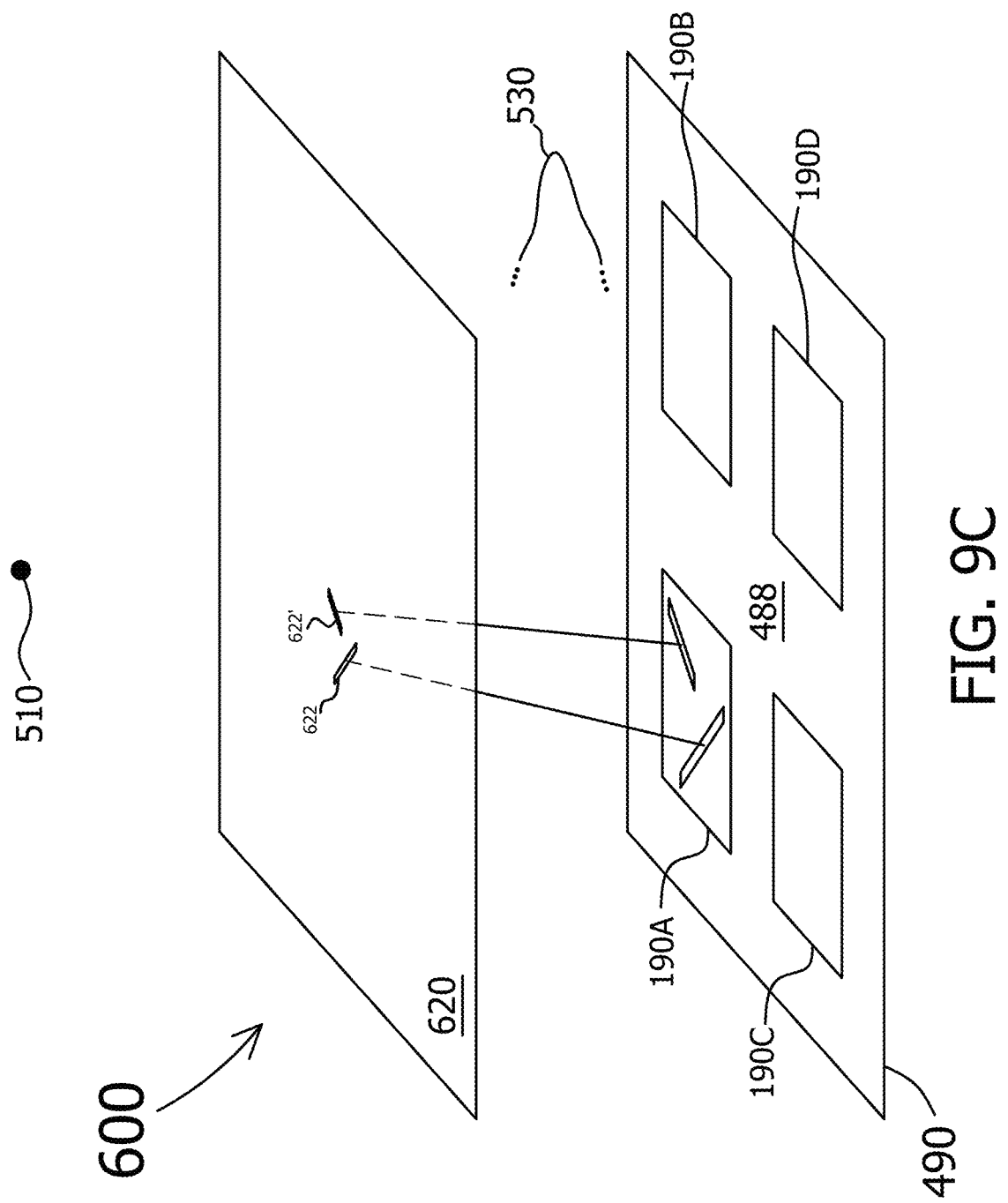

As shown in FIG. 9C, in an embodiment, during a starting exposure, the 2 fan radiation beams from the 2 slits 622 and 622' may target 2 target regions on the active area 190A of the image sensor 490 as shown.

In an embodiment, after the starting exposure, the image sensor 490 may move with the filter 620 such that during the next exposure (not shown), the 2 fan radiation beams from the 2 slits 622 and 622' target the same 2 target regions on the active area 190A. In an alternative embodiment (not shown), during the starting exposure, the 2 fan radiation beams from the slits 622 and 622' may target 2 target regions on 2 respective active areas 190 (e.g., the active areas 190A and 190B).

FIG. 9D shows a flowchart 980 generalizing and summarizing an operation of the imaging system 500 of FIG. 8A-FIG. 8C where the image sensor 490 is used in place of the radiation detector 100, according to an embodiment.

In step 982, in an embodiment, for i=1, . . . , M, a pencil radiation beam (i) (e.g., the pencil radiation beam 513*a* of FIG. 8A) may be sent incident on an incident region (i) (e.g., the incident region 513*ai* of FIG. 8A) on the image sensor 490, wherein the pencil radiation beam (i) is aimed at a target region (i) (e.g., the target region 513*at*) on the image sensor 490, wherein M is a positive integer, wherein the image sensor 490 comprises P active areas 190 (e.g., the active areas 190A-D) spatially discontinuous from each other, wherein P is an integer greater than 1, and wherein the incident regions (i), i=1, . . . , M and the target regions (i), i=1, . . . , M are on the P active areas 190.

In step 984, in an embodiment, for i=1, . . . , M, an offset (i) between the incident region (i) and the target region (i) may be determined. For example, with reference to FIG. 8A, the offset 513*ax* between the incident region 513*ai* and the target region 513*at* may be determined.

In general, in an embodiment, the operation of the imaging system 500 of FIG. 8A-FIG. 8C may be similar to the operation of the imaging system 500 of FIG. 5A-FIG. 5D.

FIG. 9E shows a flowchart 990 generalizing and summarizing an operation of the imaging system 600 of FIG. 9A-FIG. 9C where the image sensor 490 is used in place of the radiation detector 100, according to an embodiment.

In step 992, in an embodiment, first fan radiation beams (e.g., the fan radiation beams of the third exposure and the first additional exposures such as the fan radiation beam 613*a* of FIG. 6A) and second fan radiation beams (e.g., the fan radiation beams of the fourth exposure and the second additional exposures such as the fan radiation beam 613*b* of FIG. 6C) may be sent incident on the image sensor 490, wherein for i=1, . . . , M, a pair (i) of one of the first fan radiation beams (e.g., the fan radiation beam 613*a* of FIG. 6A) and one of the second fan radiation beams (e.g., the fan radiation beam 613*b* of FIG. 6C) are incident on two incident regions (e.g., the 2 incident regions 613*ai* and 613*bi* of FIG. 6E) on the image sensor 490, the two incident regions sharing a common incident region (i) (e.g., the common incident region 613*ci* of FIG. 6E) on the image sensor 490, wherein M is a positive integer, and wherein for i=1, . . . , M, the pair (i) are aimed at two target regions (e.g., the 2 target regions 613*at* and 613*bt* of FIG. 6E) on the image sensor 490, the two target regions sharing a common target region (i) (e.g., the common target region 613*ct*) on the image sensor 490, wherein the image sensor 490 comprises P active areas 190 (e.g., the 4 active areas 190A-D) spatially discontinuous from each other, wherein P is an integer greater than 1, wherein the common incident regions (i), i=1, . . . , M and the common target regions (i), i=1, . . . , M are on the P active areas 190.

In the step 994, an offset (i) between the common incident region (i) and the common target region (i) may be determined. For example, with reference to FIG. 6E & FIG. 9A, the offset 613*cx* between the common incident region 613*ci* and the common target region 613*ct* may be determined. In general, in an embodiment, the operation of the imaging system 600 of FIG. 9A-FIG. 9C may be similar to the operation of the imaging system 600 of FIG. 6A-FIG. 7G.

In an embodiment, with reference to FIG. 8A-FIG. 9C, where the image sensor 490 is used in place of the radiation detector 100 in the imaging system 500/600, the refractive index of each point of the object 530 may be determined as follows. For the case of the imaging system 500 having the image sensor 490 (FIG. 8A-FIG. 8C), in an embodiment, the refractive index of each point of the object 530 may be determined based on (A) the offsets (i), i=1, . . . , M as determined in step 984 of FIG. 9D, and (B) the positions of the target regions (i), i=1, . . . , M relative to the object 530. For the case of the imaging system 600 having the image sensor 490 (FIG. 9A-FIG. 9C), in an embodiment, the refractive index of each point of the object 530 may be determined based on (A) the offsets (i), i=1, . . . , M as determined in step 994 of FIG. 9E, and (B) the positions of the common target regions (i), i=1, . . . , M relative to the object 530.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method, comprising:
for i=1, . . . , M, sending a pencil radiation beam (i) toward an image sensor,
wherein the pencil radiation beam (i) is incident on an incident region (i) on the image sensor, wherein the pencil radiation beam (i) is aimed at a target region (i) on the image sensor, wherein M is a positive integer, wherein the image sensor comprises active areas spatially discontinuous from each other, and wherein the incident regions (i), i=1, . . . , M and the target regions (i), i=1, . . . , M are on the active areas; and for i=1, . . . , M, determining an offset (i) between the incident region (i) and the target region (i).

2. The method of claim 1, further comprising determining a refractive index for a point (i), i=1, . . . , M, of an object based on the offset (i) and a position of the target region (i) relative to the object; wherein the pencil radiation beam (i) is incident on the point (i).

3. The method of claim 1, wherein each of the target regions (i), i=1, . . . , M, is not smaller than a pixel of the image sensor.

4. The method of claim 1, wherein any two of the target regions (i), i=1, . . . , M, at the same time are spaced apart by at least 10 times of a width of a pixel of the image sensor.

5. The method of claim 1, wherein the pencil radiation beams (i), i=1, . . . , M, are formed by directing radiation through at least a pinhole of a filter, and wherein the method further comprises moving the filter and the image sensor between multiple exposures such that target regions on the image sensor the pencil radiation beams (i) are aimed at remain the same relative to the image sensor across the multiple exposures.

6. The method of claim 1, further comprising capturing images of the pencil radiation beams (i), i=1, . . . , M, determining a position (i) of the incident region (i) based on the captured image of the pencil radiation beam (i), wherein said determining the offset (i) is based on the position (i) of the incident region (i).

7. The method of claim 1, further comprising:

for i=1, . . . , M, sending additional pencil radiation beams (i, j), j=1, . . . , Ni, wherein Ni is a positive integer, and wherein each of the additional pencil radiation beams (i, j), j=1, . . . , Ni is parallel to and overlaps the pencil radiation beam (i);

capturing images of the pencil radiation beams (i), i=1, . . . , M and the additional pencil radiation beams (i, j), i=1, . . . , M, and j=1, . . . , Ni; and for i=1, . . . , M, applying a super resolution algorithm to the image of the pencil radiation beam (i) and the images of the additional pencil radiation beams (i, j), j=1, . . . , Ni thereby resulting in an enhanced image (i) of the pencil radiation beam (i), determining a position (i) of the incident region (i) based on the enhanced image (i), wherein said determining the offset (i) is based on the position (i) of the incident region (i).

8. A method, comprising:

sending first fan radiation beams and second fan radiation beams toward an image sensor, wherein for i=1, . . . , M, a pair (i) of one of the first fan radiation beams and one of the second fan radiation beams are respectively incident on two incident regions on the image sensor, the two incident regions sharing a common incident region (i) on the image sensor, wherein M is a positive integer, wherein for i=1, . . . , M, the pair (i) are respectively aimed at two target regions on the image sensor, the two target regions sharing a common target region (i) on the image sensor, wherein the image sensor comprises active areas spatially discontinuous from each other, and wherein the common incident regions (i), i=1, . . . , M and the common target regions (i), i=1, . . . , M are on the active areas; and for i=1, . . . , M, determining an offset (i) between the common incident region (i) and the common target region (i).

9. The method of claim 8, further comprising determining a refractive index for a point (i), i=1, . . . , M, of an object based on the offset (i) and a position of the common target region (i) relative to the object, wherein both fan radiation beams of the pair (i) are incident on the point (i).

10. The method of claim 8, wherein each of the common target regions (i), i=1, . . . , M, is not smaller than a pixel of the image sensor.

11. The method of claim 8, wherein any two target regions on the image sensor any two beams of the first fan radiation beams are aimed at the same time are spaced apart by at least 10 times of a width of a pixel of the image sensor.

12. The method of claim 8, wherein target regions on the image sensor aimed at by the first fan radiation beams are parallel to each other.

13. The method of claim 8, wherein the first fan radiation beams are formed by directing radiation through least a slit of a filter, and wherein the method further comprises moving the filter and the image sensor between multiple exposures such that target regions on the image sensor the first fan radiation beams are aimed at remain the same relative to the image sensor across the multiple exposures.

14. The method of claim 8, wherein target regions on the image sensor the first fan radiation beams are aimed at are not parallel to target regions on the image sensor the second fan radiation beams are aimed at.

15. The method of claim 8, wherein the first fan radiation beams are formed by directing radiation through first slits of a filter and the second fan radiation beams are formed by directing radiation through second slits of the filter, and wherein the first slits are parallel to one another, the second slits are parallel to one another and the first slits are not parallel to the second slits.

16. The method of claim 8, further comprising capturing images of the first and second fan radiation beams, determining a position (i) of the common incident region (i) based on captured images of the two beams of the pair (i), wherein said determining the offset (i) is based on the position (i) of the common incident region (i).

17. The method of claim 8, further comprising:

for each beam of the first and second fan radiation beams, sending additional fan radiation beams parallel to and overlapping said beam of the first and second fan radiation beams;

capturing images of the first and second fan radiation beams and their associated additional fan radiation beams; and for each beam of the first and second fan radiation beams, applying a super resolution algorithm to the image of said beam and the images of the additional fan radiation beams associated with said beam thereby resulting in an enhanced image of said beam,
determining a position (i) of the common incident region (i) based on the enhanced images of the two beams of the pair (i),
wherein said determining the offset (i) is based on the position (i) of the common incident region (i).

18. The method of claim 8, wherein the second fan radiation beams are sent after the first fan radiation beams are sent.

* * * * *